United States Patent [19]

Kluge et al.

[11] Patent Number: 4,558,129

[45] Date of Patent: Dec. 10, 1985

[54] BENZODIOXANYL-HYDROXYETHYLENE-PIPERAZINYL ACETANILIDES WHICH EFFECT CALCIUM ENTRY AND β-BLOCKADE

[75] Inventors: Arthur F. Kluge, Los Altos; Robin D. Clark, Palo Alto; Arthur M. Strosberg, Menlo Park, all of Calif.

[73] Assignee: Syntex (U.S.A.) Inc., Palo Alto, Calif.

[21] Appl. No.: 495,870

[22] Filed: May 18, 1983

[51] Int. Cl.[4] ............ C07D 405/06; C07D 405/12; A61K 31/495

[52] U.S. Cl. ............ 544/377; 544/400; 549/362; 549/365; 564/212; 564/305; 564/440; 564/442; 564/443; 568/27; 568/33; 568/46; 568/649; 568/650; 568/763; 568/765

[58] Field of Search ............ 544/377; 424/250

[56] References Cited

U.S. PATENT DOCUMENTS

| | | | |
|---|---|---|---|
| 2,695,294 | 11/1954 | Swain | 544/377 |
| 3,244,718 | 4/1966 | Beil | 544/377 |
| 3,360,529 | 12/1967 | Gardner | 424/278 |
| 3,488,352 | 1/1970 | Schipper | 544/377 |
| 3,496,183 | 2/1970 | Toldy et al. | 424/250 |
| 3,705,899 | 12/1972 | Regnier et al. | 544/377 |
| 3,829,441 | 8/1974 | Gardner | 424/278 |
| 3,869,459 | 3/1975 | Milkowski et al. | 424/250 |
| 3,879,401 | 4/1975 | Archibald et al. | 424/267 |
| 3,944,549 | 3/1976 | Lafon | 424/251 |
| 4,042,590 | 8/1977 | Jacquier | 544/377 |
| 4,059,621 | 11/1977 | Vincent et al. | 544/106 |
| 4,187,313 | 2/1980 | Gschwend et al. | 424/278 |
| 4,212,808 | 7/1980 | Gschwend et al. | 546/197 |
| 4,261,907 | 4/1981 | Gschwend et al. | 260/348.49 |
| 4,309,349 | 1/1982 | Gschwend et al. | 568/442 |
| 4,315,939 | 2/1982 | Frickel et al. | 424/267 |
| 4,335,126 | 6/1982 | Kleeman | 424/250 |
| 4,353,901 | 10/1982 | Clark | 424/248.57 |
| 4,353,904 | 10/1982 | Thieme et al. | 424/250 |
| 4,374,837 | 2/1983 | Favier et al. | 424/253 |

FOREIGN PATENT DOCUMENTS

| | | |
|---|---|---|
| 0025111 | 3/1981 | European Pat. Off. |
| 0068544 | 1/1983 | European Pat. Off. |
| 2942832 | 4/1980 | Fed. Rep. of Germany |
| 2267104 | 11/1975 | France |
| 2456738 | 12/1980 | France |
| 1332008 | 10/1973 | United Kingdom |
| 1387735 | 3/1975 | United Kingdom |
| 1434580 | 5/1976 | United Kingdom |
| 2067562 | 8/1979 | United Kingdom |
| 2057433 | 4/1981 | United Kingdom |

OTHER PUBLICATIONS

L. Stankeviciene et al., "Synthesis of N-Arloxy-2-Hydroxypropyl-1-Piperazines", Mater. Mezvug. Nauchv. Konf. Kaunes. Med. Inst., 25th (1976), publ. 1977, p. 322-2, [Chem. Abst. 90, 54907c (1979)].

J. M. Caroon et al., "Synthesis and Antihypertensive Activity of a Series of 8-Substituted 1-Oxa-3,8-Diazaspiro [4,5] Decan-2-Ones," J. Med. Chem., 24, 1320-1328 (1981).

R. Howe, et al., "B-Adrenegeric Blocking Agents, VII 2-(1,4-Benzodioxanyl) & 2-Chromanyl Analogs of Promethanol," [2-Isopropylamino-1-(2-Naphthylethanol],: J. Med. Chem., vol. 13, No. 2, pp. 169-176 (1970).

J. Augstein, et al., "Andrenergic Neuerone Blocking Agents Derived from 1,4-Benzodioxan," J. Med. Chem., 8, pp. 446-456 (1965).

Primary Examiner—Glennon H. Hollrah
Assistant Examiner—James H. Turnipseed
Attorney, Agent, or Firm—Grant D. Green; Tom M. Moran; Alan M. Krubiner

[57] ABSTRACT

Novel compounds of the general formula:

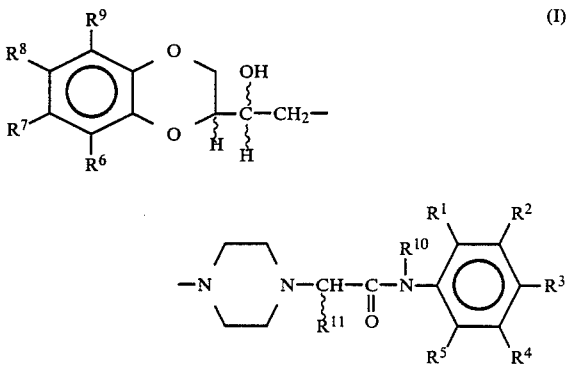

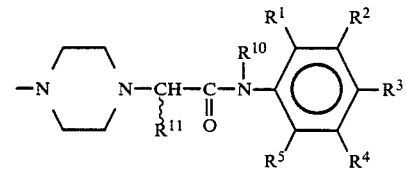

and the pharmaceutically acceptable esters and acid addition salts thereof, wherein:

$R^1$, $R^2$, $R^3$, $R^4$, $R^5$, $R^6$, $R^7$, $R^8$ and $R^9$ are each independently hydrogen, lower alkyl, lower alkoxy, trifluoromethyl, halo, lower alkylthio, lower alkyl sulfinyl, lower alkyl sulfonyl; or $R^2$ and $R^3$ together form —$OCH_2O$—; and $R^{10}$ and $R^{11}$ are each independently hydrogen or lower alkyl.

These compounds combine β-blockade and calcium entry blockade properties in the same compound and therefore are useful in therapy in the treatment of cardiovascular diseases, including hypertension, arrhythmias and variant and exercise induced angina.

13 Claims, No Drawings

BENZODIOXANYL-HYDROXYETHYLENE-PIPERAZINYL ACETANILIDES WHICH EFFECT CALCIUM ENTRY AND β-BLOCKADE

BACKGROUND OF THE INVENTION

The present invention is concerned with compounds, compositions, and methods useful for treating diseases in human beings which are affected by β-blockade and calcium entry blockade. In particular, compounds wherein piperazine is bound through one nitrogen to a benzodioxanyl moiety by a hydroxyethylene or alkanoyloxyethylene linkage, and through the other nitrogen to an acetanilide residue are useful in this regard.

Large numbers of compounds are known which affect various physiological systems related to adrenergic control. Compounds which are related to the compounds of the present invention are disclosed in Belgian Pat. No. 806,380 (U.S. Pat. No. 3,944,549), and include 1-(1,4-benzodioxan-2-ylmethyl)-4-(2,6-dimethylphenylacetanilido)piperazine; in L. Staneviciene, et al. in *Mater. Mezhvug. Nauchv. Konf. Kaunos. Med. Inst.,* 25th (1976), published in 1977, pages 322-3 [*Chem. Abstr.,* 90, 54907c (1979)]; and French Pat. No. 2,267,104. Additional references of interest in this art include U.S. Pat. Nos. 3,360,529; 3,496,183; 3,829,441; 3,879,401; 3,944,549; 4,059,621; 4,302,469; 4,315,939; 4,335,126; and 4,353,901, all of which are incorporated herein by reference. β-Adrenoreceptor blocking compounds and calcium entry blocking compounds have been used separately and in combination to mediate the symptoms of cardiovascular diseases, such as hypertension, angina and arrhythmia.

The present invention concerns a group of compounds which combine the effects of β- and calcium entry blockade in a single compound, and therefore are useful in the treatment of these cardiovascular diseases.

SUMMARY OF THE INVENTION

In one aspect this invention concerns piperazine derivatives of the general formula:

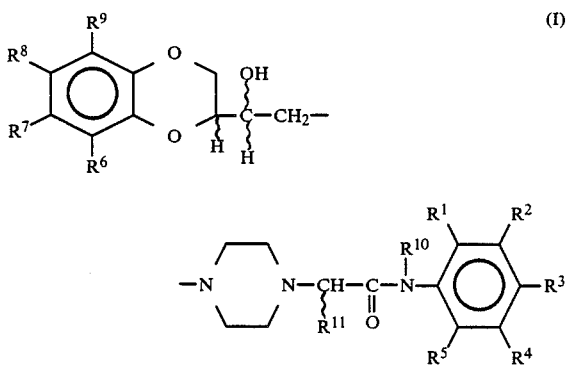

and the pharmaceutically acceptable esters and acid addition salts thereof, wherein:

$R^1$, $R^2$, $R^3$, $R^4$, $R^5$, $R^6$, $R^7$, $R^8$ and $R^9$ are each independently hydrogen, lower alkyl, lower alkoxy, trifluoromethyl, halo, lower alkylthio, lower alkyl sulfinyl or lower alkyl sulfonyl; or $R^2$ and $R^3$ together form —OCH$_2$O—; and $R^{10}$ and $R^{11}$ are each independently hydrogen or lower alkyl.

These compounds have been shown to block β-receptors in anesthetized dogs, hence in two other aspects the invention concerns a method for affecting physiological phenomena related to β-control using the compounds of formula I, and compositions for this purpose containing these compounds.

Another aspect of this invention is a process for the preparation of compounds of formula I, as described in more detail hereinafter.

DETAILED DESCRIPTION OF THE INVENTION

Definitions

As used herein:

"Diastereoisomer" refers to stereoisomers some or all of which are dissymmetric but which are not mirror images of each other. Diastereoisomers corresponding to a given structural formula must have at least two asymmetric atoms. A compound having two asymmetric atoms will usually exist in four diastereoisomeric forms, i.e. (—)-erythro, (+)-erythro, (—)-threo and (+)-threo.

"Halo" or "halogen" refers to fluoro, chloro, bromo or iodo usually regarding halo substitution for a hydrogen atom in an organic compound.

"Lower alkyl" refers to a branched or unbranched saturated hydrocarbon chain of 1–4 carbons, such as, for example, methyl, ethyl, n-propyl, i-propyl, n-butyl, i-butyl, s-butyl, t-butyl and the like.

"Lower alkoxy" refers to a group -OR wherein R is lower alkyl as herein defined.

"Lower alkylthio" refers to a group -SR wherein R is lower alkyl as herein defined.

"Lower alkyl sulfinyl" refers to

wherein R is lower alkyl as herein defined.

"Lower alkyl sulfonyl" refers to

wherein R is lower alkyl as herein defined.

"Optical isomerism" describes one type of stereoisomerism which manifests itself by the rotation that the isomer, either pure or in solution, imparts to the plane of polarized light. It is caused in many instances by the attachment of four different chemical atoms or groups to at least one of the carbon atoms in a molecule. These isomers may be described as d-, l-, or a d,l-pair or D-, L- or a D,L-pair; or R-, S-, or an R,S-pair, depending upon the nomenclature system employed.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable ester" of the compound of formula I which may be conveniently used in therapy includes those compounds containing the alkanoyloxy group [Z—C(=O)—O-], wherein Z is an alkyl group containing 1 to 12 carbon atoms, which is attached to carbon atom 2 of the ethylene linkage instead of the hydroxyl (—OH) group. The group, Z, may be, for example, methyl, ethyl, butyl, hexyl, octyl, dodecyl and the like. This invention contemplates those compounds of formula I which are esters as described herein and, at the same time, are the pharmaceutically acceptable acid addition salts thereof.

"Piperazino" structure describes the following saturated six-membered dinitrogen substituted heterocyclic moiety:

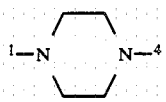

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation.

"Structure of formula I" refers to the generic structure of the compounds of the invention. The chemical bonds indicated as ( ) in formula I indicate the nonspecific stereochemistry of the asymmetric carbon atoms, e.g. at position 2 of the benzodioxanyl ring, the adjacent carbon to which is attached the hydroxyl (—OH) group, and the carbon to which $R^{11}$ is attached between the piperazine ring and the carbonyl group.

The compounds of the present invention are generally named according to the IUPAC nomenclature system. The locants for the substituents on the ring system of the above compounds of the instant invention are as depicted in the Summary of the Invention above.

For example, when $R^1$ and $R^5$ are methyl, $R^2$ to $R^4$ and $R^6$ to $R^{11}$ are hydrogen, the compound of formula I is named 1-[2-(1,4-benzodioxan-2-yl)-2-hydroxyethyl]-4-[(2,6-dimethylphenyl)aminocarbonylmethyl]piperazine, and is shown below:

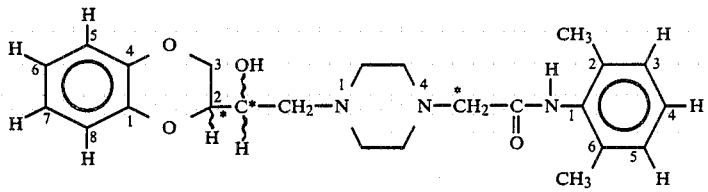

where * denotes a center or possible center of asymmetry. This compound may also be named as 1-[2-(1,4-benzodioxan2-yl)-2-hydroxyethyl]-4-(2,6-dimethylphenylcarbamoylmethyl)piperazine; or 1-[2-(1,4-benzodioxan-2-yl)-2-hydroxyethyl]4-(2,6-dimethylacetanilido)piperazine. For purposes of this patent application, the IUPAC designation first described above will be used.

The optically active compounds herein can be designated by a number of conventions; i.e., the R- and S-sequencing rules of Cahn and Prelog; erythro and threo isomers; D- and L-isomers; d- and l-isomers; and (+) and (−)-isomers, which indicates the direction a plane of polarized light is rotated by the chemical structure, either pure or in solution. These conventions are well-known in the art and are described in detail by E. L. Eliel in *Stereochemistry of Carbon Compounds*, published by McGraw Hill Book Company, Inc. of New York in 1962 and references cited therein.

Certain compounds of formula I wherein $R^{11}$ is hydrogen will have two asymetric carbon atoms, i.e. carbon atom 2 of the benzodioxanyl moiety and its adjacent non-cyclic carbon atom to which the hydroxyl group is attached. These compounds will exist in four stereochemical forms; i.e., (+)-erythro, (−)-erythro, (+)-threo and (−)-threo and mixtures thereof. Compounds of formula I where $R^{11}$ is a group other than hydrogen will have three asymmetric carbon atoms, i.e. carbon atom at the 2 position of the benzodioxanyl moiety, its adjacent noncyclic carbon atom and the carbon atom to which $R^{11}$ is attached. These compounds may exist in eight stereochemical forms and mixtures thereof. This patent application is to be interpreted to include the individual stereoisomers as well as mixtures thereof.

In the Reaction Sequences as discussed herein:

"Bzd" represents the benzodioxane moiety which may optionally be substituted by $R^6$ to $R^9$ as defined hereinabove. The linkage to other parts of the molecule is through the carbon atom at the 2 position and the other numbered positions of the benzodioxanyl group are indicated, as shown:

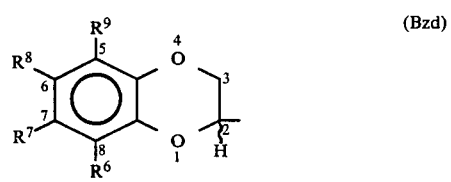

(Bzd)

"Ar" represents an optionally substituted phenyl group wherein $R^1$ to $R^5$ are as defined hereinabove, and the other numbered positions are shown.

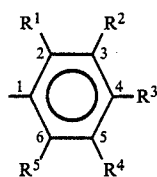

(Ar)

PREFERRED EMBODIMENTS

Embodiments of the present invention include those compounds of formula I wherein $R^1$, $R^2$ or $R^3$ are each independently methyl.

Embodiments of the present invention include those compounds of formula I wherein $R^1$, $R^2$ or $R^3$ are each independently methoxy.

Embodiments of the present invention include those compounds of formula I wherein $R^1$, $R^2$ or $R^3$ are each independently methylthio.

Embodiments of the present invention include those compounds of formula I wherein any two of the $R^1$ to $R^5$ substituents are independently methyl, thus producing the corresponding dimethylaniline derivatives.

Embodiments of the present invention include those individual compounds of formula I wherein $R^1$, $R^2$ or $R^3$ are each independently chloro, bromo or fluoro.

Presently preferred compounds of the present invention are those wherein $R^6$, $R^7$, $R^8$ and $R^9$ are each hydrogen. Particularly preferred compounds of this sub-group are those wherein $R^1$ to $R^9$ are all hydrogen.

Another presently preferred group of compounds are those wherein $R^{11}$ is hydrogen. Of this sub-group, those presently preferred are those compounds wherein all of $R^1$ to $R^9$ are hydrogen. Preferred among these are compounds wherein $R^{10}$ is also hydrogen.

Especially preferred from those compounds wherein $R^{10}$ is hydrogen are the compounds selected from the group comprising:

1-[2-(1,4-benzodioxan-2-yl)-2-hydroxyethyl]-4-[(2,6-dimethylphenyl)aminocarbonylmethyl]piperazine;
1-[2-(1,4-benzodioxan-2-yl)-2-hydroxyethyl]-4-(phenylaminocarbonylmethyl)piperazine;
1-[2-(1,4-benzodioxan-2-yl)-2-hydroxyethyl]-4-[(4-chlorophenyl)aminocarbonylmethyl]piperazine;
1-[2-(1,4-benzodioxan-2-yl)-2-hydroxyethyl]-4-[(4-methylphenyl)aminocarbonylmethyl]piperazine;
1-[2-(1,4-benzodioxan-2-yl)-2-hydroxyethyl]-4-[(4-methoxyphenyl)aminocarbonylmethyl]piperazine;
1-[2-(1,4-benzodioxan-2-yl)-2-hydroxyethyl]-4-[(2,6-dichlorophenyl)aminocarbonylmethyl]piperazine;
1-[2-(1,4-benzodioxan-2-yl)-2-hydroxyethyl]-4-[(4-trifluoromethylphenyl)aminocarbonylmethyl]piperazine;
1-[2-(6-methylsulfinyl-1,4-benzodioxan-2-yl)-2-hydroxyethyl]-4-[(phenyl)aminocarbonylmethyl]piperazine; and
1-[2-(1,4-benzodioxan-2-yl)-2-hydroxyethyl]-4-[(3,4-methylenedioxyphenyl)aminocarbonylmethyl]piperazine.

An additional set of presently preferred compounds are those wherein $R^{10}$ and $R^{11}$ are methyl; presently preferred among these is:

1-[2-(1,4-benzodioxan-2-yl)-2-hydroxyethyl]-4-[(2,6-dimethylphenyl)-N-(methyl)aminocarbonyl-1-ethyl]-piperazine.

The above embodiments and the compounds described and claimed herein also include all possible combinations of each erythro- or threo- isomer or mixtures thereof, each d- or l- (or R— and S—) optical isomer or mixtures thereof, and each pharmaceutically acceptable mono- or disubstituted acid addition salt thereof, particularly the dihydrochlorides, or mixtures thereof.

Processes for Preparation

Reaction Sequences 1, 2, 3 and 4 shown below are processes for preparing the compounds of formula I.

REACTION SEQUENCE 1

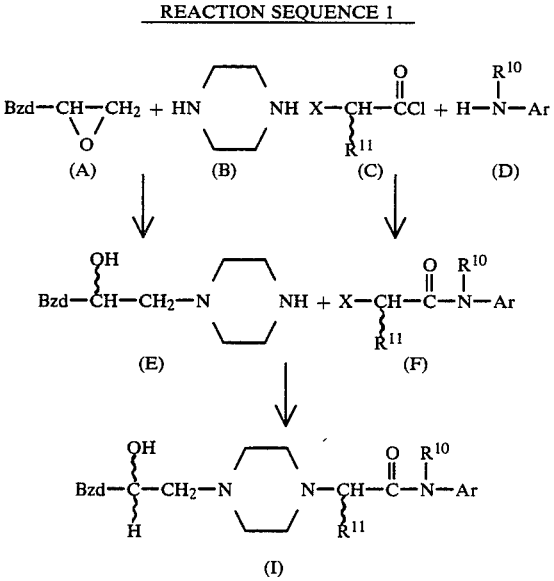

Reaction Sequence 1

The compound of formula A wherein Bzd is as described above is obtained by reacting the corresponding 2-(1,4-benzodioxan-2-yl)-1,2-dihydroxyethane with methanesulfonyl chloride or toluenesulfonyl chloride and pyridine followed by treatment with sodium hydroxide, as is well known to those in the art ([see, for example, Kluge et al., J. Med. Chem. 24, 1320 (1981)].

The intermediate 1,4-benzodioxan-2-yl epoxide compounds (formula A) are also prepared by condensing unsubstituted or substituted catechol with 2,3-bis-halomethyloxirane in the presence of a strong base, such as alkali metal hydroxides, alkoxides or hydrides, for example, sodium or potassium hydroxide, methoxide or hydride. The reaction is run in an inert solvent such as dimethylformamide, dimethylsulfoxide and the like at a temperature of about room temperature to about 100° C., preferably from about 50° to 70° C.

The catechols (or 1,2-benzenediols) are readily available or if not readily available may be prepared by methods well known in the art. 1,4-Dihalo-2,3-epoxybutane is conveniently obtained by epoxidizing the corresponding olefin, e.g., dihalides of but-2-ene-1,4-diols. The butene compound may be epoxidized with peracids such as perbenzoic acid, peracetic acid and the like or by catalytic epoxidation using air or oxygen with a catalyst such as a silver, platinum or palladium catalyst. The alkyl sulfur containing compounds, i.e., alkylthio-, alkylsulfinyl-, and alkylsulfonyl-benzodioxanes are prepared by procedures similar to those described below for the sulfur containing anilines.

When certain aryl substituted catechols are used to prepare substituted 1,4-benzodioxan-2-yl epoxides, some uncertainty may result concerning the position of the aryl substituents of the compound of formula A. When the catechol is symmetrically substituted with identical substituents, no uncertainty will exist; e.g., tetrabromocatechol, 4,5-dimethylcatechol or 3,6-dichlorocatechol, in the substituted 1,4-benzodiox-2-yl epoxide. If, however, the catechol is unsymmetrically substituted, e.g., 4-methylcatechol, the resulting compound will be a mixture of the 6-methyl and 7-methyl isomers of 1,4-benzodioxan-2-yl epoxide. If desired, these mixtures of isomers may be separated into the individual isomers using standard separation techniques, known in the art such as fractional distillation, fractional crystallization, chromatography and the like. The invention described herein encompasses the pure isomers and mixtures of these positional isomers in the compounds of formula I, the pharmaceutically acceptable salts and the therapeutic uses thereof.

The intermediate 1,4-benzodioxan-2-yl epoxide compounds may also be prepared by condensing unsubstituted or substituted salicylaldehydes or 2-hydroxyacetophenones with a 1,4-dihalo-2-butene in the presence of bases such as alkali metal hydroxides, e.g., sodium hydroxide or potassium hydroxide, or an alkali metal carbonate, e.g., sodium carbonate or potassium carbonate, in solvents such as water or ethanol. The 4-chloro-2-butenylether thus formed is reacted with a peracid such as meta-chloroperoxybenzoic acid in a solvent such as chloroform or methylene chloride at temperatures of 40° C. to 60° C. Treatment of the resulting product with an alkali metal hydroxide in a solvent mixture such as methanol/water affords the unsubstituted or substituted 1,4-benzodioxan-2-yl epoxide.

The preparation of the d,l-erythro or 2-[(2S*)-oxiranyl]-1,4-(2R*)-benzodioxan and the d,l-threo or 2-[(2R*)-2-oxiranyl]-1,4-(2R*)-benzodioxan is described by Gschwend et al. in U.S. Pat. Nos. 4,187,313; 4,212,808; 4,261,907 and 4,309,349 which are incorporated herein by reference.

These compounds of formula A can then be converted into the materials of formula E in Reaction Sequence 1 by reacting the resulting benzodioxan epoxide derivatives with piperazine (formula B), by heating in a solvent that will dissolve both reactants, using methods known to those in the art.

The compounds of formula F are prepared from the corresponding aniline, substituted aniline, or N-substituted aniline derivatives, of formula D which are commercially available, by reaction with α-haloacyl halides, such as monochloroacetyl chloride, or α-chloropropionyl chloride (compounds of formula C).

Many of the substituted anilines are commercially available. These include the methyl-, dimethyl-, trimethyl-, ethyl-, diethyl-, propyl-, butyl-, methoxy-, dimethoxy-, trimethoxy-, ethoxy-, diethoxy-, propoxy-, butoxy-, chloro-, dichloro-, trichloro-, tetrachloro-, pentachloro-, bromo-, dibromo-, tribromo-, fluoro-, difluoro-, trifluoro-, bromochloro-, bromofluoro-, chlorofluoro-, methylthio-, methylenedioxy- anilines and mixtures of the aforementioned compounds. Many N-alkylated aniline derivatives such as the N-methyl-, N-ethyl-, N-propyl- and N-butyl- anilines and substituted anilines are also commercially available according to *Chemical Sources*, published by Directories Publishing Company, Inc., Flemington, N.J. in 1979.

The methylsulfinyl and methylsulfonyl substituted anilines are prepared according to conventional procedures known in the art starting from the corresponding methylthioaniline, which is available from commercial sources. For instance, the o-methylsulfinylaniline is prepared by treating o-methylthioaniline with acetic anhydride to form the corresponding acetanilide which is then treated with sodium periodate in methanol. Upon hydrolysis to remove the acetyl group using acidic or basic conditions, there is obtained o-methylsulfinylaniline. The o-methylsulfonyl aniline is obtained by treating the acetanilide prepared above with hydrogen peroxide or 2-chloroperbenzoic acid in aqueous methanol. After hydrolysis to remove the acetyl group, there is obtained o-methylsulfonylaniline in good yield. The corresponding m- and p- substituted methylsulfinylanilines and methylsulfonylanilines are prepared by replacement of o-methylthioaniline by m-methyl and p-methylthioaniline respectively.

The corresponding ethyl-, propyl- and butylthioanilines are prepared by treatment of the commercially available aminothiophenol with sodium hydroxide followed by the appropriate alkyl iodide. The corresponding ethyl-, propyl- and butyl-sulfinyl and sulfonylanilines are prepared by replacement of o-methylthioaniline with the appropriate alkylthioaniline in the procedures described above.

Many N-alkyl substituted anilines may be prepared by procedures known in the art, such as treatment of the unsubstituted or aryl-substituted anilines described herein using an alkyl halide such as methyl chloride, ethyl chloride, propyl chloride, butyl chloride or the like in a suitable solvent such as diethylether or methylene dichloride.

Many α-halo acid halides are commercially available, including for example, chloroacetyl chloride and 2-chloropropionyl chloride. 2-Chlorobutyric acid is commercially available and may be converted to the acid chloride by methods known in the art, such as reaction with thionyl chloride or phosphorus pentachloride. The α- or 2-chloroacid chlorides which are not readily available may be prepared by conventional methods such as the Hell-Volhard-Zelinsky Reaction in which the appropriate alkyl carboxylic acid is reacted with chlorine in the presence of phosphorus. See for example, *Organic Chemistry*, by R. T. Morrison and R. N. Boyd, 2nd Edition, Ch. 18, p 604 and *Chem. Revs.*, Vol 7, p 180 (1930).

To carry out this reaction to produce compounds of formula F, the aniline derivative, a basic amine, such as triethylamine or pyridine, preferably triethylamine, and the chloroacyl chloride are dissolved in an inert aprotic organic solvent, such as, for example, benzene, chloroform, carbon tetrachloride, methylene or methylene chloride, preferably methylene chloride. The aniline and tertiary amine are in approximately equimolar amounts, and the acyl chloride is added in slight molar excess, about 1.2 or 2 molar excess, preferably 1.3 to 1.5 molar excess compared to the aniline. The mixture is cooled to about −10° C. to +10° C., preferably in an ice bath, before the addition of the acyl halide. The mixture is maintained at this low temperature for approximately 2 to 8 hours, preferably about 4 hours with stirring. The resulting condensed product, of formula F, is then isolated by conventional means.

Compounds of formula I wherein Bzd and $R^1$ to $R^{11}$ are as defined above are prepared by reacting compounds of formula E with compounds of the formula F in the presence of a solvent such as toluene/methanol mixture, ethanol and dimethylformamide and the like. The reaction mixture is heated to a temperature of about 60° C. to about 150° C., preferably to about 70° C. to about 90° C. for about 6 hours to about 24 hours.

Isolation and purification of the compounds and intermediates described can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to dryness, and the salts can be further purified by conventional methods.

The compounds of formula I produced by any of the Reaction Sequences described herein may exist as erythro and threo isomers. Accordingly, the compounds of the present invention may be prepared in either the erythro or threo forms or as mixtures thereof. Unless specified, the compounds of the instant invention are a mixture of erythro and threo forms. However, the scope of the subject invention is not considered limited to the erythro/threo mixture but encompasses the individual isomers of the subject compounds as well.

The pure erythro or threo isomers may be prepared by reacting the erythro or threo form of the intermediate epoxide (formula A) (See Gschwend references supra). If desired, a mixture of the intermediates used to prepare compounds of formula I or the final product may be separated by, e.g., recrystallization and chromatography. It is preferred to prepare the individual isomers from the isomeric intermediates of the compound of formula I.

Reaction Sequence 2

Alternatively, the compounds of formula I may be prepared according to Reaction Sequence 2 wherein Bzd, $R^1$ to $R^{11}$, Ar and X are as described above.

REACTION SEQUENCE 2

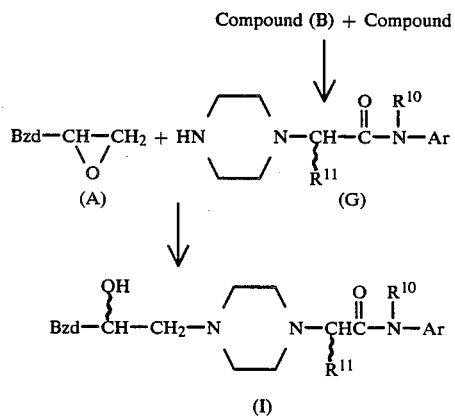

The compounds of formula F are produced by the reaction of a compound of formula C and a compound of formula D as was described above in Reaction Sequence 1.

The compounds of formula G are prepared from the corresponding compounds of formula F by reaction with piperazine (formula B), by means well known to those in the art, similar to those utilized in converting the compounds of formula E and F into compounds of formula I. In this procedure, in both cases, the halide is mixed with an excess of piperazine or a substituted piperazine, specifically a 3 to 5 molar excess, preferably about a 4 molar excess in a polar organic solvent, such as ethanol, propanol, or acetone, preferably ethanol, and the mixture is heated to 50° to 100°, preferably the reflux temperature of the solvent for 1 to 4 days, preferably about 2 days. The product of formula G may be isolated by conventional means.

The compounds of formula I are then prepared and isolated in a manner similar to that described above for the reaction of compounds of formulas A and B in Reaction Sequence 1 by combining the compounds of formulas A and G.

Reaction Sequence 3

Alternatively, the compounds of formula I may be prepared according to Reaction Sequence 3.

REACTION SEQUENCE 3

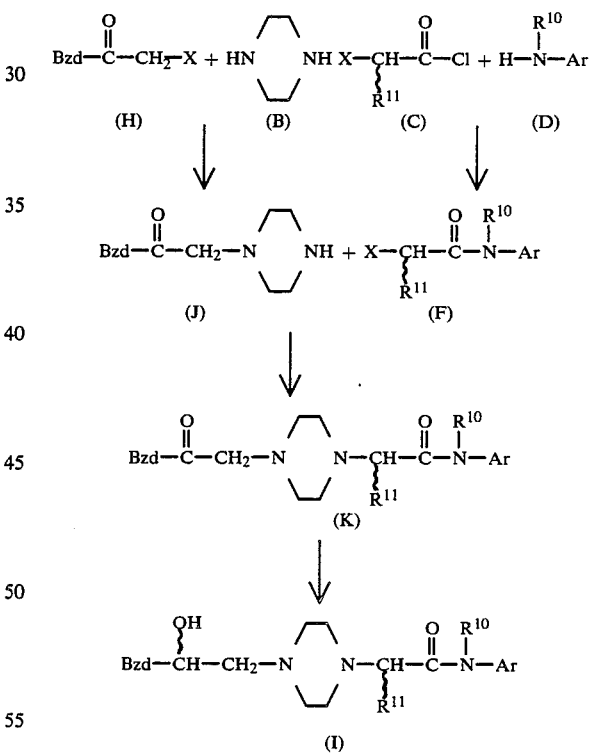

The (1,4-benzodioxan-2-yl)-α-bromomethyl ketones (formula H) are prepared by methods well known in the art, such as is described in *J. Med. Chem.*, vol. 13, 169 (1970) and *Organic Chemistry*, R. T. Morrison and R. N. Boyd, 2nd Ed., pp. 857–863, (1969).

Compounds of formula K wherein Ar, Bzd, and $R^1$ to Rhu 11 are as described above are prepared by reacting compounds of formula F with the appropriate bromoalkyl (1,4-benzodioxan-2-yl) ketone, e.g., α-bromomethyl (1,4-benzodioxan-2-yl) ketone (formula H) which has been coupled with piperazine according to methods known in the art, to give a compound of formula J, ultimately to produce the compound of formula K. The ketone intermediate of formula K that is formed is then reduced to the diastereoisomeric alcohol by methods well known in the art to yield compounds of formula I. For instance, the erythro isomer is prepared by reducing the keto compound with a metal hydride reducing agent such as sodium borohydride or lithium tri-tert-butoxy aluminum hydride.

Reaction Sequence 4

Alternatively the compounds of formula I may be prepared according to Reaction Sequence 4.

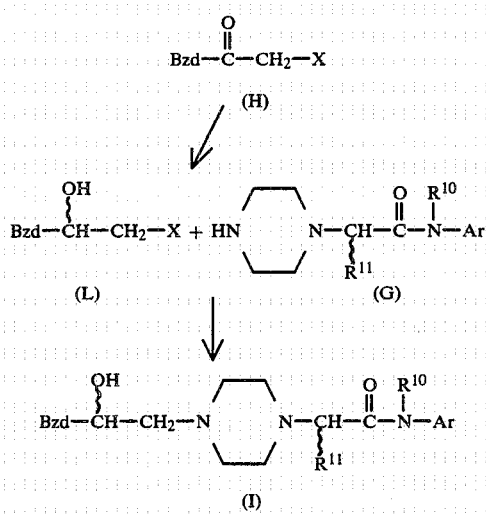

This method of preparing the compounds of formula I wherein Ar, Bzd, $R^1$ to $R^{11}$ and X are as described herein first reduces the α-bromo ketone of formula H to the corresponding diastereoisomeric alcohol of formula L and then reaction of the alcohol of formula L with compounds of formula G.

The erythro isomer of a compound of formula L is obtained by reducing the ketone with a metal hydride reducing agent such as sodium borohydride or lithium tri-tert-butoxy aluminum hydride to obtain the erythro isomer of the α-bromo alcohol.

The coupling step, usually the final step, of the processes of Reaction Sequences 1, 2, 3 and 4 is carried out in substantially similar fashion to each other. The compounds of formulas E and F or alternatively the compounds of formula A and G are combined in essentially equimolar amounts in an aprotic organic polar solvent, such as, for example, dimethylformamide, tetrahydrofuran, and the like, preferably dimethylformamide. The reaction mixture is heated to about 50° to about 100°, preferably about 60° to 70° and then the temperature raised to about 70° to 110°, preferably 85° to 95° and allowed to react for about 1 to about 24 hours, preferably overnight. The condensed product of formula I is then isolated by conventional means.

The compounds of formula I described herein may exist as mixtures of optical isomers because of the possible three asymmetric carbon atoms. Accordingly, the compounds of the present invention may be prepared in either optically active form or as racemic mixtures. Unless otherwise specified, the compounds described herein are all in the racemic form. However, the scope of the subject invention herein is not considered to be limited to a mixture of the racemic forms but to encompass all of the individual optical isomers as well.

If desired, racemic intermediates of compounds of formula A, C, E, F, G, J, K or L (supra) or final product, i.e., formula I prepared herein may be resolved into their optical antipodes by conventional resolution means known in the art, for example, by the separation (e.g., fractional crystallization) of the diastereomeric salts formed by reaction of, e.g., racemic compounds of formula I or the intermediate compounds of formula A, C, E, F, G, J, K or L (supra) with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acids, and the like and, where necessary, bases such as cinchonidine, brucine or the like. The separated pure diastereomeric salts may then be cleaved by standard means to afford the respective optical isomers of the compounds of formula I or the intermediates of formula A, C, E, F, G, J, K or L (supra).

The compounds of formula I may be isolated as free bases, but it is usually more convenient to isolate the compounds of the instant invention as acid addition salts. These salts are prepared in the usual manner, i.e., by reaction of the free base with a suitable organic or inorganic acid, for example, one of the pharmaceutically acceptable acids described above. The base of formula I, dissolved in an unreactive solvent such as an alcohol, e.g., methanol and ethanol, or an ether, e.g., diethyl ether and the like, is acidified with an acid dissolved in a like solvent. The acid solution is added until precipitation of the salt is complete. The reaction is carried out at a temperature of 20° to 50° C., preferably at room temperature. If desired, the salt can be readily converted to the free base by treatment with a base such as potassium or sodium carbonate or ammonium, potassium, or sodium hydroxide.

The compounds of formula I in free base form may be converted to the acid addition salts by treating with the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of formula I may be decomposed to the corresponding free base by treating with a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of formula I may be interchanged by taking advantage of differential solubilities and volatilities, or by treating with the appropriately loaded ion exchange resin. This conversion is carried out at a temperature between about 0° C. and the boiling point of the solvent being used as the medium for the procedure.

The pharmaceutically acceptable esters of the compound of formula I and the pharmaceutically acceptable acid addition salts thereof are prepared by treatment with an excess, about 1.0 to 2.0 equivalents of the corresponding acyl halide, or acid anhydride, in the presence of a catalyst, such as pyridine, under conditions about −10° to +10° C. for about 0.5 to 12 hr under conditions known in the art and described in Example 12 below. (See, for example, the appropriate sections of Morrison and Boyd, supra). Suitable esters which are prepared by these methods include acetates, propionates, butanoates, hexanoates, octanoates, dodecanoates, and the like. The pharmaceutically acceptable salts of the esters of the compounds of formula I are then prepared as described in Examples 8 and 12 below.

In summary then, the compounds of formula I are prepared by:

reacting an unsubstituted or substituted benzodioxan-2-yl hydroxyethylpiperazine (formula E) [which according to one alternative can be formed by the coupling of a benzodioxan-2-yl epoxide (formula A) with piperazine (formula B) to form the N-substituted piperazine (formula E)]; and the substituted halo acetanilide (formula F) [which according to one alternative can be formed by the coupling of 2-haloalkylcarboxyl halide (formula C) with the unsubstituted or substituted aniline (formula D)]. Alternatively, the compounds of formula I are prepared by:

reacting an unsubstituted or substituted benzodioxan-2-yl epoxide (formula A); and the N-substituted piperazine (formula G) [which according to one alternative can be formed by the coupling of 2-haloalkylcarboxyl-halide (formula C) with the unsubstituted or substituted aniline (formula D) to produce compound of formula F followed by coupling with piperazine (formula B)]. Alternatively, the compounds of formula I are prepared by:

reacting the N-substituted piperazine (formula J) [which according to one alternative can be formed by the coupling of an unsubstituted or substituted benzodioxan-2-yl α-halomethyl ketone (formula H) with piperazine (formula B)]; and the 2-halo (alkyl) acetanilide (formula F) [which according to one alternative can be formed by the coupling of 2-haloalkylcarboxyl halide (formula C) with unsubstituted or substituted aniline (formula D)]; to produce the benzodioxan-2-yl ketomethylene N-acetanilido piperazine (formula K) which is subsequently reduced to the compound of formula I. Alternatively, the compounds of formula I may also be prepared by:

reducing an unsubstituted or substituted benzodioxan-2-yl halomethyl ketone (formula H) to the corresponding alcohol (formula L), and coupling the compound of formula L with an N-substituted (alkyl) acetanilide piperazine (formula G) [which according to one alternative can be formed by the reaction of 2-haloalkylcarboxyl halide (formula C) with unsubstituted or substituted aniline].

Alternatively, the compound of formula I is prepared by converting a salt of formula I to a free base by using a stoichiometric excess of a base.

Alternatively, the free base of the compound of formula I is converted to a pharmaceutically acceptable acid addition salt by use of a stoichiometric excess of an acceptable acid.

Alternatively, the salt of the compound of formula I is converted to a different salt of the compound of formula I by use of a stoichiometric excess of an acceptable different acid.

UTILITY AND ADMINISTRATION

The compounds of the invention have been shown to effect β-blockade and calcium entry blockade in anesthesized dogs and in vitro animal preparations and accordingly are useful in the affecting physiological phenomena controlled by β-receptors. [See for example, Kent et al., *Federation Proceedings*, Vol. 40, 724 (1981); Killam, et al., *Federation Proceedings*, Vol. 42, 1244 (1983); and Cotten et al., *J. Pharm. Exper. Therap.*, Vol. 12, 183–190 (1957).] Among these phenomena are blood pressure, mood and heart rate (which is usually slowed). These compounds are, therefore, useful in treating a cardiovascular disease, particularly hypertension, variant and exercise-induced angina and arrhythmias, in a mammal, particularly a human being.

Administration of the active compounds and salts described herein can be via any of the accepted modes of administration for therapeutic agents which affect β-receptors. These methods include oral, parenteral, transdermal, subcutaneous and other systemic modes. The preferred method of administration is oral, except in those cases where the subject is unable to ingest, by himself, any medication. In those instances it may be necessary to administer the composition parenterally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical excipient and an active compound of formula I or the pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the severity of the affliction, the manner of administration and the judgment of the prescribing physician. However, an effective dosage is in the range of 0.1–10 mg/kg/day, preferably 0.5–5 mg/kg/day. For an average 70 kg human, this would amount to 7–700 mg per day, or preferably 35–350 mg/day.

Since all of the effects of the compounds herein (antihypertension, variant and exercise induced angina inhibition and antiarrhythmia) are achieved through the same mechanism (effecting β-blockade and calcium entry blockade in the adrenergic system) dosages (and forms of administration) are within the same general and preferred ranges for all these utilities.

For solid compositions, conventional non-toxic solid include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s), a therapeutically effective amount, i.e. in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference.

The following preparations and examples serve to illustrate the invention. They should not be construed as narrowing it, or limiting its scope.

PREPARATION A (Preparation of Compounds of formula A)

(a) To the solution of 1.32 g of catechol (1,2-benzenediol) in 15 ml of dimethylsulfoxide 0.8 g of sodium hydroxide pellets is added while stirring under nitrogen at 55° C. After about 4 hours the dark green solution is combined with 1.5 g of trans-2,3-bischloromethyloxirane and stirring is continued for 4 hours at 55°–60° C. After cooling to room temperature the mixture is diluted with 100 ml of water and extracted with diethyl ether. The extract is washed with aqueous sodium hydroxide and saturated aqueous sodium chloride, dried and evaporated to yield 1.6 g of a light yellow oil. It is chromatographed on silica gel and eluated with chloroform to yield, after evaporation, 0.9 g of a colorless oil which solidifies on standing. It is crystallized from diethyl ether to yield d,l-erythro-2-(1,4-benzodioxan-2-yl)-2-epoxide, m.p. 51°–52° C.

(b) Similarly, proceeding as in Subpart (a) above, but substituting a stoichiometrically equivalent of:
4-methyl-1,2-benzenediol;
4-n-butyl-1,2-benzenediol;
4-chloro-1,2-benzenediol;
4-bromo-1,2-benzenediol;
4-methoxy-1,2-benzenediol;
4-n-butoxy-1,2-benzenediol;
5-chloro-1,2-benzenediol;
4,5-dimethyl-1,2-benzenediol;
4,5-dichloro-1,2-benzenediol;
4-methyl-5-chloro-1,2-benzenediol;
3,4,5-trichloro-1,2-benzenediol;
3-methyl-4,5-dichloro-1,2-benzenediol;
3-methyl-4-chloro-5-methoxy-1,2-benzenediol;
3,4,5,6-tetrabromo-1,2-benzenediol;
3,6-dimethyl-4,5-dichloro-1,2-benzenediol;
4-trifluoromethyl-1,2-benzenediol;
4-methylthio-1,2-benzenediol;
4-n-butylthio-1,2-benzenediol;
4-methylsulfinyl-1,2-benzenediol;
4-n-butylsulfinyl-1,2-benzenediol;
4-methylsulfonyl-1,2-benzenediol; or
4-n-butylsulfonyl-1,2-benzenediol
for catechol, the following d,l-erythro epoxide compounds of formula A are obtained:
2-(6-methyl-1,4-benzodioxan-2-yl)-2-epoxide;
2-(6-n-butyl-1,4-benzodioxan-2-yl)-2-epoxide;
2-(6-chloro-1,4-benzodioxan-2-yl)-2-epoxide;
2-(6-bromo-1,4-benzodioxan-2-yl)-2-epoxide;
2-(6-methoxy-1,4-benzodioxan-2-yl)-2-epoxide;
2-(6-n-butoxy-1,4-benzodioxan-2-yl)-2-epoxide;
2-(7-chloro-1,4-benzodioxan-2-yl)-2-epoxide;
2-(6,7-dimethyl-1,4-benzodioxan-2-yl)-2-epoxide;
2-(6,7-dichloro-1,4-benzodioxan-2-yl)-2-epoxide;
2-(6-methyl-7-chloro-1,4-benzodioxan-2-yl)-2-epoxide;
2-(5,6,7-trichloro-1,4-benzodioxan-2-yl)-2-epoxide;
2-(5-methyl-6,7-dichloro-1,4-benzodioxan-2-yl)-2-epoxide;
2-(5-methyl-6-chloro-7-methoxy-1,4-benzodioxan-2-yl)-2-epoxide;
2-(5,6,7,8-tetrabromo-1,4-benzodioxan-2-yl)-2-epoxide;
2-(5,8-dimethyl-6,7-dichloro-1,4-benzodioxan-2-yl)-2-epoxide;
2-(6-trifluoromethyl-1,4-benzodioxan-2-yl)-2-epoxide;
2-(6-methylthio-1,4-benzodioxan-2-yl)-2-epoxide;
2-(6-n-butylthio-1,4-benzodioxan-2-yl)-2-epoxide;
2-(6-methylsulfinyl-1,4-benzodioxan-2-yl)-2-epoxide;
2-(6-n-butylsulfinyl-1,4-benzodioxan-2-yl)-2-epoxide;
2-(6-methylsulfonyl-1,4-benzodioxan-2-yl)-2-epoxide; or
2-(6-n-butylsulfonyl-1,4-benzodioxan-2-yl)-2-epoxide.
These compounds are of sufficient purity for use in Reaction Sequences 1 and 2.

(c) Similarly, proceeding as in Subpart (a) of this Preparation but substituting a stoichiometrically equivalent of cis-2,3-bischloromethyloxriane for trans-2,3-bis-chloromethyloxirane, there is obtained the d,1-threo-2-(1,4-benzodioxan-2-yl)-2-epoxide in good yield.

(d) Similarly, proceeding as in Subpart (c) of this Preparation but substituting a stoichiometrically equivalent of the substituted benzenediols cited for catechol, the corresponding d,l-threo substituted epoxide compounds of formula A are obtained.

(e) Similarly, proceeding in Subpart (a) of this Preparation but substituting a stoichiometrically equivalent amount of a mixture of cis-2,3-bischloromethyloxirane and trans-2,3-bis-chloromethyloxirane for trans-2,3-bis-chloromethyloxirane, there is obtained a corresponding mixture of dl-erythro-1,4-benzodioxan-2-yl epoxide and dl-threo-1,4-benzodioxan-2-yl epoxide in good yield.

(f) Similarly, proceeding in Subpart (b) of this Preparation but substituting a stoichiometrically equivalent amount of a mixture of cis- and trans-2,3-bischloromethyloxirane for trans-2,3-bischloromethyloxirane and an aryl substituted catechol (substituted 1,2-benzanediol) for catechol, there is obtained a corresponding mixture of dl-erythro and dl-threo-aryl-substituted-1,4-benzodioxan-2-yl epoxide in good yield.

PREPARATION B

Preparation of [(2,6-dimethylphenyl)aminocarbonylmethyl]chloride (Compound of formula F)

(a) 2,6-Dimethylaniline (96 g, 793 mmoles) and triethylamine (TEA) (96 g, 130 ml) are dissolved in one liter of methylene chloride. The mixture is cooled in ice, and the chloroacetyl chloride (89.6 g, 800 mmoles) is added slowly. The mixture is stirred for 4 hours and becomes very dark in color. The mixture is then washed with dilute hydrochloric acid, and concentrated under vacuum. Hexane is added to precipitate the product, [(2,6-dimethylphenyl)aminocarbonylmethyl]chloride, and the crude product is filtered, is washed and dried. A yield of 130 g is obtained, in sufficient purity for use in Reaction Sequences 1, 2, 3 or 4.

(b) Repeating the above procedure in a similar manner and substituting a stoichiometrically equivalent amount of:
aniline;
2-chloroaniline;
3-chloroaniline;
4-chloroaniline;
2-bromoaniline;
3-bromoaniline;
4-bromoaniline;
2-fluoroaniline;
3-fluoroaniline;
4-fluoroaniline;
2-methylaniline;
3-methylaniline;
4-methylaniline;
4-n-butylaniline;
2-methoxyaniline;
3-methoxyaniline;
4-methoxyaniline;
4-n-butoxyaniline;
2-trifluoromethylaniline;
3-trifluoromethylaniline;
4-trifluoromethylaniline;
2,6-dichloroaniline;
3,5-dimethoxyaniline;
3,4-methylenedioxyaniline;
2-chloro-5-methylaniline;
4-methylthioaniline;
4-methylsulfinylaniline;
4-methylsulfonylaniline;
4-n-butylthioaniline;
4-n-butylsulfinylaniline;
4-n-butylsulfonylaniline;
3,4-difluoroaniline;
2,5-diethoxyaniline;
2,4,5-trichloroaniline;
3,4,5-trimethoxyaniline;
2,4,5,6-tetrachloroaniline;
2,3,4,6-tetramethylaniline;
2,3,4,5,6-pentachloroaniline;
3-chloro-2,4,6-trimethylaniline;
N-methylaniline;
N-n-butylaniline;
N-methyl-2,6-dimethylaniline; or
N-n-butyl-2,6-dimethylaniline
for 2,6-dimethylaniline, there are obtained the following substituted chlorides of formula F:
(phenylaminocarbonylmethyl)chloride;
[(2-chlorophenyl)aminocarbonylmethyl]chloride;
[(3-chlorophenyl)aminocarbonylmethyl]chloride;
[(4-chlorophenyl)aminocarbonylmethyl]chloride;
[(2-bromophenyl)aminocarbonylmethyl]chloride;
[(3-bromophenyl)aminocarbonylmethyl]chloride;
[(4-bromophenyl)aminocarbonylmethyl]chloride;
[(2-fluorophenyl)aminocarbonylmethyl]chloride;
[(3-fluorophenyl)aminocarbonylmethyl]chloride;
[(4-fluorophenyl)aminocarbonylmethyl]chloride;
[(2-methylphenyl)aminocarbonylmethyl]chloride;
[(3-methylphenyl)aminocarbonylmethyl]chloride;
[(4-methylphenyl)aminocarbonylmethyl]chloride;
[(4-n-butylphenyl)aminocarbonylmethyl]chloride;
[(2-methoxyphenyl)aminocarbonylmethyl]chloride;
[(3-methoxyphenyl)aminocarbonylmethyl]chloride;
[(4-methoxyphenyl)aminocarbonylmethyl]chloride;
[(4-n-butoxyphenyl)aminocarbonylmethyl]chloride;
[(2-trifluoromethylphenyl)aminocarbonylmethyl]chloride;
[(3-trifluoromethylphenyl)aminocarbonylmethyl]chloride;
[(4-trifluoromethylphenyl)aminocarbonylmethyl]chloride;
[(2,6-dichlorophenyl)aminocarbonylmethyl]chloride;
[(3,5-dimethoxyphenyl)aminocarbonylmethyl]chloride;
[(3,4-methylenedioxyphenyl)aminocarbonylmethyl]chloride;
[(2-chloro-5-methylphenyl)aminocarbonylmethyl]chloride;
[(4-methylthiophenyl)aminocarbonylmethyl]chloride;
[(4-methylsulfinylphenyl)aminocarbonylmethyl]chloride;
[(4-methylsulfonylphenyl)aminocarbonylmethyl]chloride;
[(4-n-butylthiophenyl)aminocarbonylmethyl]chloride;
[(4-n-butylsulfinylphenyl)aminocarbonylmethyl]chloride;
[(4-n-butylsulfonylphenyl)aminocarbonylmethyl]chloride;
[(3,4-difluorophenyl)aminocarbonylmethyl]chloride;
[(2,5-diethoxyphenyl)aminocarbonylmethyl]chloride;
[(2,4,5-trichlorophenyl)aminocarbonylmethyl]chloride;
[(3,4,5-trimethoxyphenyl)aminocarbonylmethyl]chloride;
[(2,4,5,6-tetrachlorophenyl)aminocarbonylmethyl]chloride;
[(2,3,4,6-tetramethylphenyl)aminocarbonylmethyl]chloride;
[(2,3,4,5,6-pentachlorophenyl)aminocarbonylmethyl]chloride;
[(3-chloro-2,4,6-trimethylphenyl)aminocarbonylmethyl]chloride;
[N-methyl-N-(phenyl)aminocarbonylmethyl]chloride;
[N-n-butyl-N-(phenyl)aminocarbonylmethyl]chloride;
[N-methyl-N-(2,6-dimethylphenyl)aminocarbonylmethyl]chloride; or
[N-n-butyl-N-(2,6-dimethylphenyl)aminocarbonylmethyl]chloride
of sufficient purity for use in Reaction Sequences 1, 2, 3 or 4.

(c) Repeating the above procedure in Subpart (a) in a similar manner and substituting a stoichiometrically equivalent amount of
2-chloropropanoyl chloride;
2-chloro-n-butanoyl chloride; or
2-chloro-n-hexanoyl chloride
for chloroacetyl chloride, there are obtained the following substituted chlorides of formula F:
[(2,6-dimethylphenyl)aminocarbonyl-1-ethyl]chloride;
[(2,6-dimethylphenyl)aminocarbonyl-1-n-propyl]chloride; or
[(2,6-dimethylphenyl)aminocarbonyl-1-n-pentyl]chlorides of sufficient purity for use in this invention.

(d) Repeating the above procedure in Subpart (a) in a similar manner and substituting a stoichiometrically equivalent amount of 2-chloropropanoyl chloride for chloroacetyl chloride and N-methyl- or N-n-butyl-2,6-dimethylaniline for 2,6-dimethylaniline, there is obtained [N-methyl-N-(2,6-methylphenyl)aminocarbonyl-1-ethyl]chloride and [N-n-butyl-N-(2,6-methylphenyl)aminocarbonyl-1-ethyl]chloride, respectively.

(e) Repeating the above procedure of this Preparation in a similar manner and substituting a stoichiometrically equivalent amount of 2-chloro-n-hexanoyl chloride for chloroacetyl chloride and N-methyl- or N-n-butyl-2,6-dimethylaniline for 2,6-dimethylaniline, there is obtained [N-methyl-N-(2,6-methylphenyl)aminocarbonyl-1-n-pentyl]chloride or [N-n-butyl-N-(2,6-methylphenyl)aminocarbonyl-1-n-pentyl]chloride, respectively.

PREPARATION C

Preparation of 1-[(2,6-dimethylphenyl)aminocarbonylmethyl]piperazine (Compound of formula G)

(a) The crude [(2,6-dimethylphenyl)aminocarbonylmethyl]chloride, prepared in Preparation B (50 g, 0.25 mole) and piperazine (86 g, 1 mole) are dissolved in 500 ml of ethanol. The mixture is refluxed for two hours, and then cooled and evaporated. The product is harvested by adding aqueous ammonia to the residue, and extracting with methylene chloride. Three portions of methylene chloride are used, which are collected, washed with water, and evaporated to a semi-solid. Upon addition of ether, the product crystallizes and is filtered. The resulting crude mixture is boiled with ether and then evaporated to a residue and triturated with hexane to yield pure material, 1-[(2,6-dimethylphenyl)aminocarbonylmethyl]piperazine. This material is of sufficient purity for use in Reaction Sequences 2 or 4.

(b) Repeating the above procedure [Subpart (a)] in a similar manner and substituting a stoichiometrically equivalent of:
phenylaminocarbonylmethylchloride;
[(4-chlorophenyl)aminocarbonylmethyl]chloride;
[(4-methylphenyl)aminocarbonylmethyl]chloride;
[(4-methoxyphenyl)aminocarbonylmethyl]chloride;
[(3-chlorophenyl)aminocarbonylmethyl]chloride;
[(2,6-dichlorophenyl)aminocarbonylmethyl]chloride;
[(2,4,6-trimethylphenyl)aminocarbonylmethyl]chloride;
[(3,5-dimethoxyphenyl)aminocarbonylmethyl]chloride;
[(4-methylthiophenyl)aminocarbonylmethyl]chloride;
[(4-n-butylthiophenyl)aminocarbonylmethyl]chloride;
[(4-methylsulfinylphenyl)aminocarbonylmethyl]chloride;
[(4-n-butylsulfinylphenyl)aminocarbonylmethyl]chloride;
[(4-methylsulfonylphenyl)aminocarbonylmethyl]chloride;
[(4-n-butylsulfonylphenyl)aminocarbonylmethyl]chloride;
[(4-trifluoromethylphenyl)aminocarbonylmethyl]chloride;
[(2-chloro-5-methylphenyl)aminocarbonylmethyl]chloride;
[(3,5-difluorophenyl)aminocarbonylmethyl]chloride;
[(2,6-diethoxyphenyl)aminocarbonylmethyl]chloride;
[(3-bromo-4-ethylphenyl)aminocarbonylmethyl]chloride;
[(4-n-butylphenyl)aminocarbonylmethyl]chloride;
[(4-isobutylphenyl)aminocarbonylmethyl]chloride;
[(3,4,5-trimethoxyphenyl)aminocarbonylmethyl]chloride;
[(2,3,4,5-tetrachlorophenyl)aminocarbonylmethyl]chloride;
[(2,3,4,5,6-pentachlorophenyl)aminocarbonylmethyl]chloride;
[N-methyl-N-(2,6-dimethylphenyl)aminocarbonylmethyl]chloride;
[N-n-butyl-N-(2,6-dimethylphenyl)aminocarbonylmethyl]chloride;
[(2,6-dimethylphenyl)aminocarbonyl-1-ethyl]chloride;
[N-methyl-N-(2,6-dimethylphenyl)aminocarbonyl-1-ethyl]chloride;
[N-n-butyl-N-(2,6-dimethylphenyl)aminocarbonyl-1-ethyl]chloride; or
[(2,6-dimethylphenyl)aminocarbonyl-1-n-pentyl]chloride;
N-methyl-N-(2,6-dimethylphenyl)aminocarbonyl-1-n-pentyl]chloride; or
N-n-butyl-N-(2,6-dimethylphenyl)aminocarbonyl-1-n-pentyl]chloride for [(2,6-dimethylphenyl)aminocarbonylmethyl]chloride, there are obtained the following piperazines:
1-(phenylaminocarbonylmethyl)piperazine;
1-[4-chlorophenyl)aminocarbonylmethyl]piperazine;
1-[(4-methylphenyl)aminocarbonylmethyl]piperazine;
1-[(4-methoxyphenyl)aminocarbonylmethyl]piperazine;
1-[(3-chlorophenyl)aminocarbonylmethyl]piperazine;
1-[(2,6-dichlorophenyl)aminocarbonylmethyl]piperazine;
1-[(2,4,6-trimethylphenyl)aminocarbonylmethyl]piperazine;
1-[(3,5-dimethoxyphenyl)aminocarbonylmethyl]piperazine;
1-[(4-methylthiophenyl)aminocarbonylmethyl]piperazine;
1-[(4-n-butylthiophenyl)aminocarbonylmethyl]piperazine;
1-[(4-methylsulfinylphenyl)aminocarbonylmethyl]piperazine;
1-[(4-n-butylsulfinylphenyl)aminocarbonylmethyl]piperazine;
1-[(4-methylsulfonylphenyl)aminocarbonylmethyl]piperazine;
1-[(4-n-butylsulfonylphenyl)aminocarbonylmethyl]piperazine;
1-[(4-trifluoromethylphenyl)aminocarbonylmethyl]piperazine;
1-[(2-chloro-5-methylphenyl)aminocarbonylmethyl]piperazine;
1-[(3,5-difluorophenyl)aminocarbonylmethyl]piperazine;

1-[(2,6-diethoxyphenyl)aminocarbonylmethyl]piperazine;
1-[(3-bromo-4-ethylphenyl)aminocarbonylmethyl]piperazine;
1-[(4-n-butylphenyl)aminocarbonylmethyl]piperazine;
1-[(4-isobutylphenyl)aminocarbonylmethyl]piperazine;
1-[(3,4,5-trimethoxyphenyl)aminocarbonylmethyl]piperazine;
1-[(2,3,4,5-tetrachlorophenyl)aminocarbonylmethyl]piperazine;
1-[(2,3,4,5,6-pentachlorophenyl)aminocarbonylmethyl]piperazine;
1-[N-methyl-N-(2,6-dimethylphenyl)aminocarbonylmethyl]piperazine;
1-[N-n-butyl-N-(2,6-dimethylphenyl)aminocarbonylmethyl]piperazine;
1-[(2,6-dimethylphenyl)aminocarbonyl-1-ethyl]piperazine;
1-[N-methyl-N-(2,6-dimethylphenyl)aminocarbonyl-1-ethyl]piperazine;
1-[N-n-butyl-N-(2,6-dimethylphenyl)aminocarbonyl-1-ethyl]piperazine;
1-[(2,6-dimethylphenyl)aminocarbonyl-1-n-pentyl]piperazine;
1-[N-methyl-N-(2,6-dimethylphenyl)aminocarbonyl-1-n-pentyl]piperazine; or
1-[N-n-butyl-N-(2,6-dimethylphenyl)aminocarbonyl-1-n-pentyl]piperazine in sufficient purity for use in Reaction Sequences 2 and 4.

PREPARATION D

Preparation of 1-[2-(1,4-benzodioxan-2-yl)-2-hydroxyethyl]piperazine (Compound of formula E)

(a) In a manner similar to that described in Subpart (a) of Preparation C, but substituting 2-(1,4-benzodioxan-2-yl)-2-epoxide for the starting chloride and refluxing for 6 hours rather than two days, one obtains the corresponding compound of formula E, namely 1-[2-(1,4-benzodioxan-2-yl)-2-hydroxyethyl]piperazine.

(b) Repeating the above procedure [Subpart (a)] in a similar manner and substituting a stoichiometrically equivalent of:
2-(6-methyl-1,4-benzodioxan-2-yl)-2-epoxide;
2-(6-methoxy-1,4-benzodioxan-2-yl)-2-epoxide;
2-(6-chloro-1,4-benzodioxan-2-yl)-2-epoxide;
2-(6-bromo-1,4-benzodioxan-2-yl)-2-epoxide;
2-(7-n-butyl-1,4-benzodioxan-2-yl)-2-epoxide;
2-(7-n-butoxy-1,4-benzodioxan-2-yl)-2-epoxide;
2-(7-chloro-1,4-benzodioxan-2-yl)-2-epoxide;
2-(6,7-dimethyl-1,4-benzodioxan-2-yl)-2-epoxide;
2-(6,7-dichloro-1,4-benzodioxan-2-yl)-2-epoxide;
2-(5,6,7-trichloro-1,4-benzodioxan-2-yl)-2-epoxide;
2-(5-methyl-6-chloro-7-methoxy-1,4-benzodioxan-2-yl)-2-epoxide;
2-(5,6,7,8-tetrabromo-1,4-benzodioxan-2-yl)-2-epoxide;
2-(5,8-dimethyl-6,7-dichloro-1,4-benzodioxan-2-yl)-2-epoxide;
2-(6-trifluoromethyl-1,4-benzodioxan-2-yl)-2-epoxide;
2-(6-methylthio-1,4-benzodioxan-2-yl)-2-epoxide;
2-(6-methylsulfinyl-1,4-benzodioxan-2-yl)-2-epoxide;
2-(6-methylsulfonyl-1,4-benzodioxan-2-yl)-2-epoxide;
2-(6-n-butylthio-1,4-benzodioxan-2-yl)-2-epoxide;
2-(6-n-butylsulfinyl-1,4-benzodioxan-2-yl)-2-epoxide; or
2-(6-n-butylsulfonyl-1,4-benzodioxan-2-yl)-2-epoxide
   for   1-[(2,6-dimethylphenyl)aminocarbonylmethyl]chloride,
there are obtained the following piperazines:
1-[2-(6-methyl-1,4-benzodioxan-2-yl)-2-hydroxyethyl]piperazine;
1-[2-(6-methoxy-1,4-benzodioxan-2-yl)-2-hydroxyethyl]piperazine;
1-[2-(6-chloro-1,4-benzodioxan-2-yl)-2-hydroxyethyl]piperazine;
1-[2-(6-bromo-1,4-benzodioxan-2-yl)-2-hydroxyethyl]piperazine;
1-[2-(7-n-butyl-1,4-benzodioxan-2-yl)-2-hydroxyethyl]piperazine;
1-[2-(7-n-butoxy-1,4-benzodioxan-2-yl)-2-hydroxyethyl]piperazine;
1-[2-(7-chloro-1,4-benzodioxan-2-yl)-2-hydroxyethyl]piperazine;
1-[2-(6,7-dimethyl-1,4-benzodioxan-2-yl)-2-hydroxyethyl]-piperazine;
1-[2-(6,7-dichloro-1,4-benzodioxan-2-yl)-2-hydroxyethyl]piperazine;
1-[2-(5,6,7-trichloro-1,4-benzodioxan-2-yl)-2-hydroxyethyl]piperazine;
1-[2-(5-methyl-6-chloro-7-methoxy-1,4-benzodioxan-2-yl)-2-hydroxyethyl]piperazine;
1-[2-(5,6,7,8-tetrabromo-1,4-benzodioxan-2-yl)-2-hydroxyethyl]piperazine;
1-[2-(5,8-dimethyl-6,7-dichloro-1,4-benzodioxan-2-yl)-2-hydroxyethyl]piperazine;
1-[2-(6-trifluoromethyl-1,4-benzodioxan-2-yl)-2-hydroxyethyl]piperazine;
1-[2-(6-methylthio-1,4-benzodioxan-2-yl)-2-hydroxyethyl]piperazine;
1-[2-(6-methylsulfinyl-1,4-benzodioxan-2-yl)-2-hydroxyethyl]piperazine;
1-[2-(6-methylsulfonyl-1,4-benzodioxan-2-yl)-2-hydroxyethyl]piperazine;
1-[2-(6-n-butylthio-1,4-benzodioxan-2-yl)-2-hydroxyethyl]piperazine;
1-[2-(6-n-butylsulfinyl-1,4-benzodioxan-2-yl)-2-hydroxyethyl]piperazine; or
1-[2-(6-n-butylsulfonyl-1,4-benzodioxan-2-yl)-2-hydroxyethyl]piperazine.

(c) Repeating the above procedure [Subpart (a)] in a similar manner and substituting a stoichiometrically equivalent of d,l-erythro-[2-(1,4-benzodioxan-2-yl)]-2-epoxide for [2-(1,4-benzodioxan-2-yl)]-2-epoxide, one obtains the corresponding d,l-erythro-[2-(1,4-benzodioxan-2-yl)-2-hydroxyethyl]piperazine.

(d) Repeating the above procedure [Subpart (a)] in a similar manner and substituting a stoichiometrically equivalent of one of the d,l-erythro-[2-(substituted-1,4-benzodioxan-2-yl)]-2-epoxides of Preparation A [Subpart (b)] for [2-(1,4-benzodioxan-2-yl)]-2-epoxide, one obtains the corresponding d,l-erythro-[2-(substituted-1,4-benzodioxan-2-yl)-2-hydroxyethyl]piperazine.

(e) Repeating the above procedure [Subpart (a)] in a similar manner and substituting a stoichiometrically equivalent of d,l-threo-[2-(1,4-benzodioxan-2-yl)]-2-epoxide for [2-(1,4-benzodioxan-2-yl)-2-epoxide, one obtains the corresponding d,l-threo-[2-(1,4-benzodioxan-2-yl)-2-hydroxyethyl]piperazine.

(f) Repeating the above procedure [Subpart (a)] in a similar manner and substituting a stoichiometrically equivalent of any one of the d,l-threo-[2-(substituted-1,4-benzodioxan-2-yl)-2-epoxides in Preparation A [Subpart (d)] for [2-(1,4-benzodioxan-2-yl)]-2-epoxide, one obtains the corresponding, d,l-threo-[2-(substituted-1,4-benzodioxan-2-yl)-2-hydroxyethyl]piperazine.

(g) Repeating the above procedure [Subpart (a)] in a similar manner and substituting a stoichiometrically equivalent amount of a mixture of any one of the d,l-erythro and d,l-threo-(unsubstituted or aryl substituted-1,4-benzodioxan-2-yl)-2-epoxides of Preparation A [Subparts (e) or (f)] for [2-(1,4-benzodioxan-2-yl)]-2-epoxide, one obtains the corresponding mixture of d,l-erythro and d,l-threo-[2-(unsubstituted or aryl substituted-1,4-benzodioxan-2-yl)-2-hydroxyethyl]piperazine in good yield.

PREPARATION E

Preparation of compounds of formula J (a) Fifty g of bromomethyl 1,4-benzodioxan-2-yl ketone (prepared according to *J. Med. Chem.*, 13, 169 (1970)), and 85 g of piperazine (ALDRICH) are dissolved in 450 ml of ethanol. After refluxing for 6 hr the mixture is cooled and evaporated. The product is recovered by addition of aqueous ammonia and extraction with three 100 ml portions of methylene chloride washed with water and evaporated to a semisolid. After addition of diethyl ether, the crude product crystallizes and is filtered. The resulting mixture is boiled in diethyl ether, evaporated to a residue and triturated with hexane to yield 21 g of 1-[(1,4-benzodioxan-2-yl)-2-carbonylmethyl]piperazine. This material is of sufficient purity to use in Reaction Sequences 3 and 4.

(b) Repeating the above procedure in [Subpart (a)] in a similar manner and substituting a stoichiometrically equivalent of:
bromomethyl (6-methyl-1,4-benzodioxan-2-yl) ketone;
bromomethyl (6-methoxy-1,4-benzodioxan-2-yl) ketone;
bromomethyl (6-chloro-1,4-benzodioxan-2-yl) ketone;
bromomethyl (7-methyl-1,4-benzodioxan-2-yl) ketone;
bromomethyl (7-methoxy-1,4-benzodioxan-2-yl) ketone;
bromomethyl (7-chloro-1,4-benzodioxan-2-yl) ketone;
bromomethyl (6,7-dichloro-1,4-benzodioxan-2-yl) ketone;
bromomethyl (6-methyl-7-chloro-1,4-benzodioxan-2-yl) ketone;
bromomethyl (5,6,7-trichloro-1,4-benzodioxan-2-yl) ketone;
bromomethyl (5-methyl-6,7-dichloro-1,4-benzodioxan-2-yl) ketone;
bromomethyl (5-methyl-6-chloro-7-methoxy-1,4-benzodioxan-2-yl) ketone;
bromomethyl (5,8-dimethyl-6,7-dichloro-1,4-benzodioxan-2-yl) ketone;
bromomethyl (5,6,7,8-tetrabromo-1,4-benzodioxan-2-yl) ketone;
bromomethyl (6-trifluoromethyl-1,4-benzodioxan-2-yl) ketone;
bromomethyl (6-methylthio-1,4-benzodioxan-2-yl) ketone;
bromomethyl (6-n-butylthio-1,4-benzodioxan-2-yl) ketone;
bromomethyl (6-methylsulfinyl-1,4-benzodioxan-2-yl) ketone;
bromomethyl (6-n-butylsulfinyl-1,4-benzodioxan-2-yl) ketone;
bromomethyl (6-methylsulfonyl-1,4-benzodioxan-2-yl) ketone; or
bromomethyl (6-n-butylsulfonyl-1,4-benzodioxan-2-yl) ketone
for bromomethyl 1,4-benzodioxan-2-yl ketone, there are obtained the following piperazines:
1-[(6-methyl-1,4-benzodioxan-2-yl)-2-carbonylmethyl]piperazine;
1-[(6-methoxy-1,4-benzodioxan-2-yl)-2-carbonylmethyl]piperazine;
1-[(6-chloro-1,4-benzodioxan-2-yl)-2-carbonylmethyl]piperazine;
1-[(7-methyl-1,4-benzodioxan-2-yl)-2-carbonylmethyl]piperazine;
1-[(7-methoxy-1,4-benzodioxan-2-yl)-2-carbonylmethyl]piperazine;
1-[(7-chloro-1,4-benzodioxan-2-yl)-2-carbonylmethyl]piperazine;
1-[(6,7-dichloro-1,4-benzodioxan-2-yl)-2-carbonylmethyl]piperazine;
1-[(6-methyl-7-chloro-1,4-benzodioxan-2-yl)-2-carbonylmethyl]piperazine;
1-[(5,6,7-trichloro-1,4-benzodioxan-2-yl)-2-carbonylmethyl]piperazine;
1-[(5-methyl-6,7-dichloro-1,4-benzodioxan-2-yl)-2-carbonylmethyl]piperazine;
1-[(5-methyl-6-chloro-7-methoxy-1,4-benzodioxan-2-yl)-2-carbonylmethyl]piperazine;
1-[(5,8-dimethyl-6,7-dichloro-1,4-benzodioxan-2-yl)-2-carbonylmethyl]piperazine;
1-[(5,6,7,8-tetrabromo-1,4-benzodioxan-2-yl)-2-carbonylmethyl]piperazine;
1-[(6-trifluoromethyl-1,4-benzodioxan-2-yl)-2-carbonylmethyl]piperazine;
1-[(6-methylthio-1,4-benzodioxan-2-yl)-2-carbonylmethyl]piperazine;
1-[(6-n-butylthio-1,4-benzodioxan-2-yl)-2-carbonylmethyl]piperazine;
1-[(6-methylsulfinyl-1,4-benzodioxan-2-yl)-2-carbonylmethyl]piperazine;
1-[(6-n-butylsulfinyl-1,4-benzodioxan-2-yl)-2-carbonylmethyl]piperazine;
1-[(6-methylsulfonyl-1,4-benzodioxan-2-yl)-2-carbonylmethyl]piperazine; or
1-[(6-n-butylsulfonyl-1,4-benzodioxan-2-yl)-2-carbonylmethyl]piperazine.

EXAMPLE 1

Preparation of 1-[2-(1,4-benzodioxan-2-yl)-2-hydroxyethyl]-4-[(2,6-dimethylphenyl)aminocarbonylmethyl]piperazine (Reaction Sequence 1)

(a) The [(2,6-dimethylphenyl)aminocarbonylmethyl]chloride from Preparation B [Subpart (a)] (12.9 g, 65 mmoles) and 1-[2-(1,4-benzodioxan-2-yl)-2-hydroxyethyl]piperazine from Preparation D [Subpart (g)] (15 g, 65 mmoles) are mixed in 100 ml of dimethylformamide. The mixture is stirred at 65° C. to dissolve the components, and then at 90° C. overnight. The entire mixture is added to water and acidified with hydrochloric acid. The resulting homogeneous mixture is washed with ether, and then made basic with ammonia, and extracted with three portions of methylene chloride. The methylene chloride extracts, which contained the product, are washed with water twice, and then evaporated to 28 g of an oil. The oil is purified by chromatographing with 500 g of silica gel with 5% methanol in methylene chloride. The 20 g of yellow oil which are obtained are dissolved in methanol and crystallized by the addition of hydrochloric acid. Precipitation is completed by addition of ether and 16 g of the product, 1-[2-(1,4-benzodioxan-2-yl)-2-hydroxyethyl]-4-[(2,6-dimethylphenyl)aminocarbonylmethyl]piperazine, is obtained as an oil.

Because the 1-[2-(1,4-benzodioxan-2-yl)-2-hydroxyethyl]piperazine from Preparation D has undefined stereochemistry at the carbon atom at the 2 ring position, this compound and the substituted compounds of Subparts (b), (c) and (d) below are obtained as a mixture of the d,l-erythro and d,l-threo forms.

(b) Similarly, proceeding as in Subpart (a) above but substituting a stoichiometrically equivalent of any one of the optionally substituted chloride compounds prepared in Preparation B above for 1-[(2,6-dimethylphenyl)aminocarbonylmethyl]chloride, there is obtained the corresponding 1-[2-(1,4-benzodioxan-2-yl)-2-hydroxyethyl]-4-[(optionally substituted-phenyl)aminocarbonylalkyl]piperazine.

Exemplary compounds are as follows:

1-[2-(1,4-benzodioxan-2-yl)-2-hydroxyethyl]-4-(phenylaminocarbonylmethyl)piperazine;
1-[2-(1,4-benzodioxan-2-yl)-2-hydroxyethyl]-4-[4-chlorophenyl)aminocarbonylmethyl]piperazine;
1-[2-(1,4-benzodioxan-2-yl)-2-hydroxyethyl]-4-[(4-methylphenyl)aminocarbonylmethyl]piperazine;
1-[2-(1,4-benzodioxan-2-yl)-2-hydroxyethyl]-4-[(4-methoxyphenyl)aminocarbonylmethyl]piperazine;
1-[2-(1,4-benzodioxan-2-yl)-2-hydroxyethyl]-4-[(4-bromophenyl)aminocarbonylmethyl]piperazine;
1-[2-(1,4-benzodioxan-2-yl)-2-hydroxyethyl]-4-[(3,4-methylenedioxyphenyl)aminocarbonylmethyl]piperazine;
1-[2-(1,4-benzodioxan-2-yl)-2-hydroxyethyl]-4-[(2,6-dichlorophenyl)aminocarbnylmethyl]piperazine;
1-[2-(1,4-benzodioxan-2-yl)-2-hydroxyethyl]-4-[(2,4,6-trimethylphenyl)aminocarbonylmethyl]piperazine;
1-[2-(1,4-benzodioxan-2-yl)-2-hydroxyethyl]-4-[(3,4,5-dimethoxyphenyl)aminocarbonylmethyl]piperazine;
1-[2-(1,4-benzodioxan-2-yl)-2-hydroxyethyl]-4-[(4-methylthiophenyl)aminocarbonylmethyl]piperazine;
1-[2-(1,4-benzodioxan-2-yl)-2-hydroxyethyl]-4-[(4-ethylthiophenyl)aminocarbonylmethyl]piperazine;
1-[2-(1,4-benzodioxan-2-yl)-2-hydroxyethyl]-4-[(4-methylsulfinylphenyl)aminocarbonylmethyl]piperazine;
1-[2-(1,4-benzodioxan-2-yl)-2-hydroxyethyl]-4-[(4-n-propylsulfinylphenyl)aminocarbonylmethyl]piperazine;
1-[2-(1,4-benzodioxan-2-yl)-2-hydroxyethyl]-4-[(4-trifluoromethylphenyl)aminocarbonylmethyl]piperazine;
1-[2-(1,4-benzodioxan-2-yl)-2-hydroxyethyl]-4-1-[(2-chloro-5-methylphenyl)aminocarbonylmethyl]piperazine;
1-[2-(1,4-benzodioxan-2-yl)-2-hydroxyethyl]-4-[(3,5-difluorophenyl)aminocarbonylmethyl]piperazine;
1-[2-(1,4-benzodioxan-2-yl)-2-hydroxyethyl]-4-[(2,6-diethoxyphenyl)aminocarbonylmethyl]piperazine;
1-[2-(1,4-benzodioxan-2-yl)-2-hydroxyethyl]-4-[(3-bromo-4-ethylphenyl)aminocarbonylmethyl]piperazine;
1-[2-(1,4-benzodioxan-2-yl)-2-hydroxyethyl]-4-[(4-n-butylphenyl)aminocarbonylmethyl]piperazine;
1-[2-(1,4-benzodioxan-2-yl)-2-hydroxyethyl]-4-[(4-isobutylphenyl)aminocarbonylmethyl]piperazine;
1-[2-(1,4-benzodioxan-2-yl)-2-hydroxyethyl]-4-[(2,6-dimethylphenyl)aminocarbonyl-1-ethyl]piperazine;
1-[2-(1,4-benzodioxan-2-yl)-2-hydroxyethyl]-4-[N-methyl-N-(2,6-dimethylphenyl)aminocarbonyl-1-ethyl]piperazine;
1-[2-(1,4-benzodioxan-2-yl)-2-hydroxyethyl]-4-[N-n-butyl-N-(2,6-dimethylphenyl)aminocarbonyl-1-ethyl]piperazine;
1-[2-(1,4-benzodioxan-2-yl)-2-hydroxyethyl]-4-[(2,6-dimethylphenyl)aminocarbonyl-1-n-pentyl]piperazine;
1-[2-(1,4-benzodioxan-2-yl)-2-hydroxyethyl]-4-[N-methyl-N-(2,6-dimethylphenyl)aminocarbonyl-1-n-pentyl]piperazine; or
1-[2-(1,4-benzodioxan-2-yl)-2-hydroxyethyl]-4-[N-n-butyl-N-(2,6-dimethylphenyl)aminocarbonyl-1-n-pentyl]piperazine.

(c) Similarly, proceeding as in Subpart (a) above but substituting a stoichiometrically equivalent of any one of the substituted piperazine compounds described in Preparation D [Subpart (b)] above for 2-[(1,4-benzodioxan-2-yl)-2-hydroxyethyl]piperazine, there is obtained the corresponding 1-[2-(substituted-1,4-benzodioxan-2-yl)-2-hydroxyethyl]-4-[(2,6-dimethylphenyl)aminocarbonylmethyl]piperazine.

Exemplary compounds include the following:

1-[2-(6-methyl-1,4-benzodioxan-2-yl)-2-hydroxyethyl]-4-[(2,6-dimethylphenyl)aminocarbonylmethyl]piperazine;
1-[2-(6-methoxy-1,4-benzodioxan-2-yl)-2-hydroxyethyl]-4-[(2,6-dimethylphenyl)aminocarbonylmethyl]piperazine;
1-[2-(6-chloro-1,4-benzodioxan-2-yl)-2-hydroxyethyl]-4-[(2,6-dimethylphenyl)aminocarbonylmethyl]piperazine;
1-[2-(7-methyl-1,4-benzodioxan-2-yl)-2-hydroxyethyl]-4-[(2,6-dimethylphenyl)aminocarbonylmethyl]piperazine;
1-[2-(7-methoxy-1,4-benzodioxan-2-yl)-2-hydroxyethyl]-4-[(2,6-dimethylphenyl)aminocarbonylmethyl]piperazine;
1-[2-(7-chloro-1,4-benzodioxan-2-yl)-2-hydroxyethyl]-4-[(2,6-dimethylphenyl)aminocarbonylmethyl]piperazine; and
1-[2-(6,7-dimethyl-1,4-benzodioxan-2-yl)-2-hydroxyethyl]-4-[(2,6-dimethylphenyl)aminocarbonylmethyl]piperazine.

(d) Similarly, proceeding as in [Subpart (a)] above but substituting a stoichiometrically equivalent of any one of the optionally substituted chloride compounds described in Preparation B [Subpart (b)] above for 1-[(2,6-dimethylphenyl)aminocarbonylmethyl]chloride and also substituting a stoichiometrically equivalent of any one of the optionally substituted piperazine compounds described in Preparation D [(Subpart (b)] above for 1-[2-(1,4-benzodioxan-2-yl)-2-hydroxyethyl]piperazine, there is obtained the corresponding 1-[2-(optionally substituted-1,4-benzodioxan-2-yl)-2-hydroxyethyl]-4-[(optionally substituted phenyl)aminocarbonylmethyl]piperazine.

Exemplary compounds are as follows:

1-[2-(6-methyl-1,4-benzodioxan-2-yl)-2-hydroxyethyl]-4-(phenylaminocarbonylmethyl)piperazine;
1-[2-(6-chloro-1,4-benzodioxan-2-yl)-2-hydroxyethyl]-4-[(4-chlorophenyl)aminocarbonylmethyl]piperazine;
1-[2-(6-methyl-1,4-benzodioxan-2-yl)-2-hydroxyethyl]-4-[(4-methylphenyl)aminocarbonylmethyl]piperazine;

1-[2-(6-methoxy-1,4-benzodioxan-2-yl)-2-hydroxyethyl]-4-[(4-methoxyphenyl)aminocarbonylmethyl]piperazine;

1-[2-(6,7-dimethyl-1,4-benzodioxan-2-yl)-2-hydroxyethyl]-4-[(4-chlorophenyl)aminocarbonylmethyl]piperazine;

1-[2-(6-methoxy-1,4-benzodioxan-2-yl)-2-hydroxyethyl]-4-[(3-chlorophenyl)aminocarbonylmethyl]piperazine;

1-[2-(6-methoxy-1,4-benzodioxan-2-yl)-2-hydroxyethyl]-4-[(2,6-dichlorophenyl)aminocarbonylmethyl]piperazine;

1-[2-(6-methoxy-1,4-benzodioxan-2-yl)-2-hydroxyethyl]-4-[(2,4,6-trimethylphenyl)aminocarbonylmethyl]piperazine;

1-[2-(6-methylthio-1,4-benzodioxan-2-yl)-2-hydroxyethyl]-4-[(3,5-dimethoxyphenyl)aminocarbonylmethyl]piperazine;

1-[2-(7-chloro-1,4-benzodioxan-2-yl)-2-hydroxyethyl]-4-[(4-methylthiophenyl)aminocarbonylmethyl]piperazine;

1-[2-(7-methyl-1,4-benzodioxan-2-yl)-2-hydroxyethyl]-4-[(4-ethylthiophenyl)aminocarbonylmethyl]piperazine;

1-[2-(7-methoxy-1,4-benzodioxan-2-yl)-2-hydroxyethyl]-4-[4-methylsulfinylphenyl)aminocarbonylmethyl]piperazine;

1-[2-(6-trifluoromethyl-1,4-benzodioxan-2-yl)-2-hydroxyethyl]-4-[(4-n-butylsulfinylphenyl)aminocarbonylmethyl]piperazine;

1-[2-(6-methyl-1,4-benzodioxan-2-yl)-2-hydroxyethyl]-4-[(4-trifluoromethylphenyl)aminocarbonylmethyl]piperazine;

1-[2-(6-methylsulfinyl-1,4-benzodioxan-2-yl)-2-hydroxyethyl]-4-[(phenyl)aminocarbonylmethyl]piperazine;

1-[2-(6-methylsulfonyl-1,4-benzodioxan-2-yl)-2-hydroxy-ethyl]-4-[(3,5-difluorophenyl)aminocarbonylmethyl]piperazine;

1-[2-(6-n-butylsulfinyl-1,4-benzodioxan-2-yl)-2-hydroxy-ethyl]-4-[(2,6-diethoxyphenyl)aminocarbonylmethyl]piperazine;

1-[2-(6-methoxy-1,4-benzodioxan-2-yl)-2-hydroxyethyl]-4-[(3-bromo-4-ethylphenyl)aminocarbonylmethyl]piperazine;

1-[2-(6-methylthio-1,4-benzodioxan-2-yl)-2-hydroxyethyl]-4-[(4-n-butylphenyl)aminocarbonylmethyl]piperazine;

1-[2-(7-methoxy-1,4-benzodioxan-2-yl)-2-hydroxyethyl]-4-[(4-isobutylphenyl)aminocarbonylmethyl]piperazine;

1-[2-(6-n-butylthio-1,4-benzodioxan-2-yl)-2-hydroxyethyl]-4-[(2,6-dimethylphenyl)aminocarbonylmethyl]piperazine;

1-[2-(5-methyl-6,7-dichloro-1,4-benzodioxan-2-yl)-2-hydroxyethyl]-4-[(2,6-dimethylphenyl)aminocarbonylmethyl]piperazine;

1-[2-(5,6,7,8-tetrachloro-1,4-benzodioxan-2-yl)-2-hydroxyethyl]-4-[(2,6-dimethylphenyl)aminocarbonylmethyl]piperazine;

1-[2-(5-methyl-6-chloro-1,4-benzodioxan-2-yl)-2-hydroxyethyl]-4-[(2,6-dimethylphenyl)aminocarbonylmethyl]piperazine;

1-[2-(7-n-butylsulfinyl-1,4-benzodioxan-2-yl)-2-hydroxyethyl]-4-[(2,6-dimethylphenyl)aminocarbonylmethyl]piperazine;

1-[2-(7-n-butylsulfonyl-1,4-benzodioxan-2-yl)-2-hydroxyethyl]-4-[(2,6-dimethylphenyl)aminocarbonylmethyl]piperazine; or 1-[2-(6,7-dimethyl-1,4-benzodioxan-2-yl)-2-hydroxyethyl]-4-[(2,6-dimethylphenyl)aminocarbonylmethyl]piperazine.

(e) Similarly, proceeding as in Subpart (a) above but substituting a stoichiometrically equivalent of d,l-erythro- or any one of the substituted d,l-erythro-2-[(1,4-benzodioxan-2-yl)-2-hydroxyethyl]piperazine compounds described above in Preparation D [Subparts (c) and (d)] for 2-[(1,4-benzodioxan-2-yl)-2-hydroxyethyl]piperazine, and also substituting a stoichiometrically equivalent of any one of the substituted phenyl aminocarbonylmethyl chloride compounds described in Preparation B above for 1-[(2,6-dimethylphenyl)aminocarbonylmethyl]chloride, there is obtained the corresponding d,l-erythro-[2-(substituted-1,4-benzodioxan-2-yl)-2-hydroxyethyl]-4-[(substituted phenyl)aminocarbonylmethyl]piperazine.

(f) Similarly, proceeding as in Subpart (a) above, but substituting the appropriately substituted 1,4-benzodioxan-2-yl epoxide for 1,4-benzodioxan-2-yl epoxide, the following compounds are prepared:

1-[2-(6-methyl-1,4-benzodioxan-2-yl)-2-hydroxyethyl]-4-[2,6-dimethylphenyl)aminocarbonylmethyl]piperazine;

1-[2-(6-methoxy-1,4-benzodioxan-2-yl)-2-hydroxyethyl]-4-[2,6-dimethylphenyl)aminocarbonylmethyl]piperazine;

1-[2-(6-chloro-1,4-benzodioxan-2-yl)-2-hydroxyethyl]-4-[2,6-dimethylphenyl)aminocarbonylmethyl]piperazine;

1-[2-(7-methyl-1,4-benzodioxan-2-yl)-2-hydroxyethyl]-4-[2,6-dimethylphenyl)aminocarbonylmethyl]piperazine;

1-[2-(7-methoxy-1,4-benzodioxan-2-yl)-2-hydroxyethyl]-4-[2,6-dimethylphenyl)aminocarbonylmethyl]piperazine;

1-[2-(7-chloro-1,4-benzodioxan-2-yl)-2-hydroxyethyl]-4-[(2,6-dimethylphenyl)aminocarbonylmethyl]piperazine; or 1-[2-(6,7-dimethyl-1,4-benzodioxan-2-yl)-2-hydroxyethyl]-4-[(2,6-dimethylphenyl)aminocarbonylmethyl]piperazine.

Additional exemplary compounds of the d,l-erythro form are described in Subparts (b), (c), (d) and (e) of this example.

(g) Similarly, proceeding as in Subpart (a) above substituting a stoichiometrically equivalent amount of d,l-threo or any one of the substituted d,l-threo-2-[1,4-benzodioxan-2-yl)-2-hydroxyethyl]piperazine compounds described in Preparation D [Subpart (f)] for 2-[(1,4-benzodioxan-2-yl)-2-hydroxyethyl]piperazine and also substituting a stoichiometrically equivalent of any one of the substituted phenyl aminocarbonylmethyl chloride compounds described in Preparation B [Subpart (b)] above for 1-[(2,6-dimethylphenyl)aminocarbonylmethyl]chloride, there is obtained the corresponding d,l-threo-[2-(substituted-1,4-benzodioxan-2-yl)-2-hydroxyethyl]-4-(substituted-phenyl)aminocarbonylmethyl]piperazine.

Additional exemplary compounds then having the dl-erythro and d,l-threo forms as a mixture are named in Subparts (b), (c), (d) (e), and (f) of this example.

(h) Similarly, proceeding as in Subpart (a) above substituting a stoichiometrically equivalent amount of a mixture of d,l-erythro and d,l-threo or any one of the substituted d,l-erythro and d,l-threo-2-[1,4-benzodioxan-2-yl)-2-hydroxyethyl]piperazine compounds described in Preparation D [Subpart (g)] for 2-[(1,4-benzodioxan-2-yl)-2-hydroxyethyl]piperazine and also substituting a stoichiometrically equivalent of any one of the substituted phenyl aminocarbonylmethyl chloride compounds described in Preparation B [Subpart (b)] above for 1-[(2,6-dimethylphenyl)aminocarbonylmethyl]chloride, there is obtained the corresponding mixture of d,l-erythro and d,l-threo-[2-(substituted-1,4-benzodioxan-2-yl)-2-hydroxyethyl]-4-(substituted-phenyl-)aminocarbonylmethyl]piperazine.

Additional exemplary compounds then having the dl-erythro and d,l-threo forms as a mixture are named in Subparts (b), (c), (d), (e), and (f) of this example.

EXAMPLE 2

Preparation of 1-[2-(1,4-benzodioxan-2-yl)-2-hydroxyethyl]-4-[(2,6-dimethylphenyl)aminocarbonylmethyl]piperazine (Reaction Sequence 2)

(a) Substituting into the procedure of Example 1, 1-[(2,6-dimethylphenyl)aminocarbonylmethyl]piperazine rather than the corresponding chloride, and 2-[(1,4-benzodioxan-2-yl)-2-epoxide, rather than the corresponding piperazine, one obtains the 1-[2-(1,4-benzodioxan-2-yl)-2-hydroxyethyl]-4-[(2,6-dimethylphenyl-)aminocarbonylmethyl]piperazine compound.

Because the 2-[1,4-benzodioxan-2-yl)-2-epoxide from Preparation A has undefined stereochemistry at the carbon atom at position 2 of the ring, this compound and the substituted compounds of Subparts (b), (c) and (d) below are obtained as a mixture of the d,l-erythro and d,l-threo forms.

(b) Similarly, proceeding as in Subpart (a) above but substituting a stoichiometrically equivalent of any one of the substituted phenyl piperazine compounds described in Preparation C above for 1-[(2,6-dimethylphenyl)aminocarbonylmethyl]piperazine, there is obtained the corresponding 1-[2-(1,4-benzodioxan-2-yl)-2-hydroxyethyl]-4-[(substituted phenyl)aminocarbonylmethyl]piperazine.

Exemplary compounds are described in Example 1 [Subpart (b)] above.

(c) Similarly, proceeding as in Subpart (a) above but substituting a stoichiometrically equivalent amount of any one of the substituted 2-(1,4-benzodioxan-2-yl-2-epoxide compounds described in Preparation A, [Subpart (b)] above for 2-(1,4-benzodioxan-2-yl)-2-epoxide, there is obtained the corresponding 1-[(substituted-1,4-benzodioxan-2-yl)-2-hydroxyethyl]-4-[(2,6-dimethylphenyl)aminocarbonylmethyl]piperazine.

Exemplary compounds are described in Example 1 [Subpart (c)] above.

(d) Similarly, proceeding as in Subpart (a) above but substituting a stoichiometrically equivalent of any one of the substituted phenyl piperazine compounds described in Preparation C above for 1-[(2,6-dimethylphenyl)aminocarbonylmethyl]piperazine, and substituting a stoichiometrically equivalent of any one of the substituted benzodioxan-2-yl epoxides described in Preparation A above for 2-[(1,4-benzodioxan-2-yl)-2-epoxide, there is obtained the corresponding 1-[2-(substituted-1,4-benzodioxan-2-yl)-2-hydroxyethyl]-4-[(substituted phenyl)aminocarbonylmethyl]piperazine.

Exemplary compounds are described in Example 1 [Subpart (d)] above.

(e) Similarly, proceeding as in Subpart (a) above but substituting a stoichiometrically equivalent of d,l-erythro- or any one of the substituted d,l-erythro forms of the 2-(1,4-benzodioxan-2-yl)-2-epoxide from Preparation A above, and also substituting a stoichiometrically equivalent of any one of the substituted phenyl piperazine compounds described in Preparation C above for 1-[(2,6-dimethylphenyl)aminocarbonylmethyl]piperazine, there is obtained the corresponding d,l-erythro-[2-(substituted-1,4-benzodioxan-2-yl)-2-hydroxyethyl]-4-[(substituted phenyl)aminocarbonylmethyl]piperazine.

Exemplary compounds of the d,l-erythro form are described in Example 1, Subparts (b), (c) and (d) above.

(f) Similarly, proceeding as in Subpart (a) above but substituting a stoichiometrically equivalent of d,l-threo- or any one of the substituted d,l-threo-2-[(1,4-benzodioxan-2-yl)-2-epoxide compounds described in Preparation A above for 2-[(1,4-benzodioxan-2-yl)-2-epoxide, and also substituting a stoichiometrically equivalent of any one of the substituted phenylaminocarbonyl chloride compounds described in Preparation B [Subpart (b)] above for 1-[(2,6-dimethylphenyl)aminocarbonylmethyl]chloride, there is obtained the corresponding d,l-threo-[2-(substituted-1,4-benzodioxan-2-yl)-2-hydroxyethyl]-4-[(substituted phenyl)aminocarbonylmethyl]piperazine.

(g) Exemplary compounds of the d,l-threo form are described in Example 1, Subparts (b), (c) and (d) above.

EXAMPLE 3

Preparation of 1-[2-(1,4-benzodioxan-2-yl)-2-hydroxyethyl]-4-[(2,6-dimethylphenyl)aminocarbonylmethyl]piperazine (Reaction Sequence 3)

(a) The [(2,6-dimethylphenyl)aminocarbonylmethyl]chloride of Preparation B (12.6 g) and 2-[(1,4-benzodioxan-2-yl)-2-carbonylmethyl]piperazine (Compound J) (15 g) are mixed in 105 ml of dimethylformamide. The mixture is stirred at about 65°–70° C. to dissolve the components, and about 90° C. overnight. The mixture is added to water and ice (about 100 ml), acidified with hydrochloric acid, washed with ether made basic with ammonia and extracted with three 100 ml portions of methylene chloride. The methylene chloride extracts are combined, washed with two 50 ml portions of water and evaporated to a tan oil weighing 27 g, which is purified by chromatography using 500 g of silica gel using 5% methanol/methylene chloride as eluent. The 19 g of yellow oil which are obtained are dissolved in methanol and crystallized using ether to produce 15 g of 1-[2-(1,4-benzodioxan-2-yl)-2-carbonylmethyl]-4-[(2,6-dimethylphenyl) aminocarbonylmethyl]piperazine (Compound K).

Sodium borohydride (2.0 g) is added during one hour to a stirred solution of Compound K and in methanol (200 ml) at 0° C. After 24 hours the methanol is evaporated and water is added and the product (Compound I) is isolated as the dihydrochloride by extraction from diethyl ether, m.p. 175°–176° C.

(b) Exemplary compounds of formula I are produced in Subpart (a) by replacement of the compound of formula J with its substituted analogs and also by replacement of the compound of formula B with its substituted analogs.

Additional exemplary compounds are described in Example 1, Subparts (b), (c), (d) and (e).

EXAMPLE 4

Preparation of
1-[2-(1,4-benzodioxan-2-yl)-2-hydroxyethyl]-4-[(2,6-dimethylphenyl) aminocarbonylmethyl]piperazine
(Reaction Sequence 4)

(a) 1-(1,4-Benzodioxan-2-yl)-2-bromoethanol (formula H) (12 g) prepared according to *J. Med. Chem.* 13, 169, (1970), is treated with 1-[(2,6-dimethylphenyl)aminocarbonylmethyl]piperazine (14 g) in 500 ml of ethanol. The remainder of the procedure is described in Example 1 above and 21 g of the 1-[2-(1,4-benzodioxan-2-yl)-2-hydroxyethyl]-4-[(2,6-dimethylphenyl)aminocarbonylmethyl]piperazine is obtained from hexane. The dihydrochloride salt has a melting point of 175°–176° C.

(b) Exemplary compounds of formula I are produced by the replacement of the compound of formula H with its substituted analogs and also by the replacement of the compound of formula B with its substituted analogs. Additional exemplary compounds of formula I are described in Example 1, Subparts (b), (c), (d), (e), (f) and (g).

EXAMPLE 5

(Preparation of Compounds of formula I)

(a) A solution of 0.70 g. of 1-[(2,6-dimethylphenyl)aminocarbonylmethyl]piperazine and 0.71 g of the d,l-erythro-2-(1,4-benzodioxan-2-yl)-2-epoxide in 20 ml of toluene and 20 ml of methanol is refluxed for 12 hours. Evaporation and chromatography of the residue on silica gel with 10% methanol-methylene chloride gives 0.5 g. of d,l-erythro-1-[2-(1,4-benzodioxan-2-yl)-2-hydroxyethyl]-4-[(2,6-dimethylphenyl)aminocarbonylmethyl]piperazine which is then dissolved in methanol containing excess HCl and precipitated with ether to give the di HCl salt.

(b) Similarly, proceeding as in Subpart (a) above, but substituting the appropriate 1-(substituted arylaminocarbonylmethyl)piperazine from Preparation C for 4-[(2,6-dimethylphenyl)aminocarbonylmethyl]piperazine, the following exemplary compounds are prepared as the dihydrochloride salts:

d,l-erythro-1-[2-(1,4-benzodioxan-2-yl)-2-hydroxyethyl]-4-(phenylaminocarbonylmethyl)piperazine;

d,l-erythro-1-[2-(1,4-benzodioxan-2-yl)-2-hydroxyethyl]-4-[(4-chlorophenyl)aminocarbonylmethyl]piperazine;

d,l-erythro-1-[2-(1,4-benzodioxan-2-yl)-2-hydroxyethyl]-4-[(4-methylphenyl)aminocarbonylmethyl]piperazine;

d,l-erythro-1-[2-(1,4-benzodioxan-2-yl)-2-hydroxyethyl]-4-[(4-methoxyphenyl)aminocarbonylmethyl]piperazine;

d,l-erythro-1-[2-(1,4-benzodioxan-2-yl)-2-hydroxyethyl]-4-[(4-chlorophenyl)aminocarbonylmethyl]piperazine; and d,l-erythro-1-[2-(1,4-benzodioxan-2-yl)-2-hydroxyethyl]-4-[(3-chlorophenyl)aminocarbonylmethyl]piperazine.

EXAMPLE 6

Preparation of Salts of Compounds of formula I (a) A solution of 0.70 g. of 1-[2,6-dimethylphenyl)aminocarbonylmethyl]piperazine and 0.71 g of the 1,4-benzodioxan-2-yl epoxide in 20 ml of toluene and 20 ml of methanol is refluxed for 12 hours. Evaporation and chromatography of the residue on silica gel with 10% methanol-methylene chloride gives 0.5 g of 1-[2-(1,4-benzodioxan-2-yl)-2-hydroxyethyl]-4-[(2,6-dimethylphenyl)aminocarbonylmethyl]piperazine which is then dissolved in methanol containing excess HCl and precipitated with ether to give the di HCl salt.

(b) Similarly, proceeding as in Subpart (a) above, but substituting the appropriate 1-(substituted arylaminocarbonylmethyl)piperazine from Preparation C for 1-[(2,6-dimethylphenyl)aminocarbonylmethyl]piperazine, the exemplary compounds are prepared as the dihydrochloride salts.

EXAMPLE 7

(a) Similarly, the compounds of formula I produced using any of the procedures of Examples 1, 2, 3, 4 or 5 above, the following compounds may be prepared as the hydrochloride or dihydrochloride salts using the procedure of Examples 5 or 6. If desired, following the exemplary compounds and salts may be converted into the free base form by the procedure in Examples 9 and 11 or to another salt by following the procedure of Example 10.

1-[2-(1,4-benzodioxan-2-yl)-2-hydroxyethyl]-4-(phenylaminocarbonylmethyl)piperazine and dihydrochloride;

1-[2-(1,4-benzodioxan-2-yl)-2-hydroxyethyl]-4-[(4-chlorophenyl)aminocarbonylmethyl]piperazine and dihydrochloride;

1-[2-(1,4-benzodioxan-2-yl)-2-hydroxyethyl]-4-[(4-methylphenyl)aminocarbonylmethyl]piperazine and dihydrochloride;

1-[2-(1,4-benzodioxan-2-yl)-2-hydroxyethyl]-4-[(4-methoxyphenyl)aminocarbonylmethyl]piperazine and dihydrochloride;

1-[2-(1,4-benzodioxan-2-yl)-2-hydroxyethyl]-4-[(2,6-dichlorophenyl)aminocarbonylmethyl]piperazine and dihydrochloride;

1-[2-(1,4-benzodioxan-2-yl)-2-hydroxyethyl]-4-[(2,6-dimethylphenyl)aminocarbonylmethyl]piperazine and dihydrochloride salt, (d,l-erythro, di-HCl, m.p. 175°–176° C.);

1-[2-(1,4-benzodioxan-2-yl)-2-hydroxyethyl]-4-[(3,5-dimethoxyphenyl)aminocarbonylmethyl]piperazine and dihydrochloride;

1-[2-(1,4-benzodioxan-2-yl)-2-hydroxyethyl]-4-[(2-chloro-5-methylphenyl)aminocarbonylmethyl]piperazine and dihydrochloride;

1-[2-(1,4-benzodioxan-2-yl)-2-hydroxyethyl]-4-[(4-thiomethylphenyl)aminocarbonylmethyl]piperazine and dihydrochloride;

1-[2-(1,4-benzodioxan-2-yl)-2-hydroxyethyl]-4-[(4-n-propylsulfinylphenyl)aminocarbonylmethyl]piperazine and dihydrochloride;

1-[2-[6-chloro-1,4-benzodioxan-2-yl)-2-hydroxyethyl]-4-[(3,5-difluorophenyl)aminocarbonylmethyl]piperazine and dihydrochloride;

1-[2-(7-ethyl-1,4-benzodioxan-2-yl)-2-hydroxyethyl]-4-[phenylaminocarbonylmethyl]piperazine and dihydrochloride;

1-[2-(1,4-benzodioxan-2-yl)-2-hydroxyethyl]-4-[(2,6-diethoxyphenyl)aminocarbonylmethyl]piperazine and dihydrochloride;

1-[2-(1,4-benzodioxan-2-yl)-2-hydroxyethyl]-4-[(3-bromo-4-ethylphenyl)aminocarbonylmethyl]piperazine and dihydrochloride;

1-[2-(6-methoxy-1,4-benzodioxan-2-yl)-2-hydroxyethyl]-4-(phenylaminocarbonylmethyl)piperazine and dihydrochloride;

1-[2-(5-n-butyl-1,4-benzodioxan-2-yl)-2-hydroxyethyl]-4-[phenylaminocarbonylmethyl]piperazine and dihydrochloride;

1-[2-(1,4-benzodioxan-2-yl)-2-hydroxyethyl]-4-[N-methyl-N-(2,6-diethoxyphenyl)aminocarbonylmethyl]piperazine and dihydrochloride; or 1-[2-(1,4-benzodioxan-2-yl)-2-hydroxyethyl]-4-[4-methylthiophenyl)aminocarbonylmethyl]piperazine and dihydrochloride.

(b) Similarly, proceeding as in Subpart (a) above, but substituting an equivalent amount of erythro- or threo-(1,4-benzodioxan-2-yl)epoxide for 1,4-benzodioxan-2-yl)epoxide, there is obtained the corresponding salt derivatives having the erythro- or threo- orientation, respectively.

(c) Similarly, proceeding as in Subpart (a) above, but substituting an equivalent amount of substituted erythro- or threo-(1,4-benzodioxan-2-yl)epoxide for threo-1,4-benzodioxan-2-yl)epoxide, there is obtained the corresponding salt derivatives having the corresponding erythro- or threo-orientation, respectively. The erythro and threo epoxides are described in U.S. Pat. No. 4,212,808.

EXAMPLE 8

Conversion of Free Base to Salt 8.0 g of 1-[2-(1,4-benzodioxan-2-yl)-2-hydroxyethyl]-4-[(2,6-dimethylphenyl)aminocarbonylmethyl]piperazine is dissolved in methanol and acidified with methanolic hydrochloric acid. The precipitate is washed with ether to give 7.0 g of the dihydrochloride salt of 1-[2-(1,4-benzodioxan-2-yl)-2-hydroxyethyl]-4-[(2,6-dimethylphenyl)aminocarbonylmethyl]piperazine, (d,l-erythro, m.p. 175°-176° C.).

In similar manner, all compounds of formula I in base form prepared in accordance with Examples 1, 2, 3, or 4 can be converted to the corresponding pharmaceutically acceptable acid addition salts by treatment with the appropriate acid, for example, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

EXAMPLE 9

Conversion of Salt to Free Base 1.0 g of 1-[2-(1,4-benzodioxan-2-yl)-2-hydroxyethyl]-4-[(2,6-dimethylphenyl)aminocarbonylmethyl]piperazine 2HCl suspended in 50 ml of ether is stirred with excess dilute aqueous potassium carbonate solution until the salt is completely dissolved. The organic layer is then separated, washed twice with water, dried over magnesium sulfate and evaporated to yield 1-[2-(1,4-benzodioxan-2-yl)-2-hydroxyethyl]-4-[(2,6-dimethylphenyl)aminocarbonylmethyl]piperazine as the free base.

In a similar manner, the acid addition salts prepared in accordance with Example 8 are converted to the corresponding free base.

EXAMPLE 10

Direct Interchange of Acid Addition Salts

1-[2-(1,4-benzodioxan-2-yl)-2-hydroxyethyl]-4-[(2,6-dimethylphenyl)aminocarbonylmethyl]piperazine acetate (1.0 g) is dissolved in 50 ml 50% aqueous sulfuric acid, and the solution evaporated to dryness. The product is suspended in ethanol and filtered, air dried and recrystallized from methanol/acetone to yield 1-[2-(1,4-benzodioxan-2-yl)-2-hydroxyethyl]-4-[(2,6-dimethylphenyl)aminocarbonylmethyl]piperazine .2HSO$_4$.

EXAMPLE 11

Conversion of Salt to Free Base

A solution of 3.5 g of 1-[2-(1,4-benzodioxan-2-yl)ethyl]-4-[(2,6-dimethylphenyl)aminocarbonylmethyl]piperazine dihydrochloride salt in water (50 ml) is adjusted to pH 12 with ammonium hydroxide solution and extracted with methylene chloride. The methylene chloride is evaporated to afford 3 g of 1-[2-(1,4-benzodioxan-2-yl)-2-hydroxyethyl]-4-[(2,6-dimethylphenyl)aminocarbonylmethyl]piperazine as the free base.

In a similar manner, the acid addition salts prepared in accordance with Example 8 are converted to the corresponding free base.

EXAMPLE 12

Preparation of Esters and Dihydrochloride Salts of Formula I (a) One g of 1-[2-(1,4-benzodioxan-2-yl)-2-hydroxyethyl]-4-[(2,6-dimethylphenyl)aminocarbonylmethyl]piperazine is dissolved in 15 ml of pyridine and cooled in an ice bath to 0°-5° C. Acetic anhydride (0.6 g) is slowly added and the reaction mixture is stirred for 2 hr. After the addition of 100 ml of water, the reaction mixture is extracted twice with 100-ml portions of diethylether. After combining, the ether portion is washed twice with 100 ml of water and evaporated to dryness to produce 1-[2-(1,4-benzodioxan-2-yl)-2-acetoxyethyl]-4-[(2,6-dimethylphenyl)aminocarbonylmethyl]piperazine as an oil.

(b) Repeating the procedure of Subpart (a) of this Example in a similar manner and substituting a stoichiometrically equivalent amount of propanoic anhydride;

n-butanoic anhydride;

n-hexanoic anhydride;

n-octanoic anhydride; or n-dodecanoic anhydride for acetic anhydride, there are obtained the following piperazines:

1-[2-(1,4-benzodioxan-2-yl)-2-propanoyloxyethyl]-4-[(2,6-dimethylphenyl)aminocarbonylmethyl]piperazine;

1-[2-(1,4-benzodioxan-2-yl)-2-n-butanoyloxyethyl]-4-[(2,6-dimethylphenyl)aminocarbonylmethyl]piperazine;

1-[2-(1,4-benzodioxan-2-yl)-2-n-hexanoyloxyethyl]-4-[(2,6-dimethylphenyl)aminocarbonylmethyl]piperazine;

1-[2-(1,4-benzodioxan-2-yl)-2-n-octanoyloxyethyl]-4-[(2,6-dimethylphenyl)aminocarbonylmethyl]piperazine; and 1-[2-(1,4-benzodioxan-2-yl)-2-n-dodecanoyloxyethyl]-4-[(2,6-dimethylphenyl)aminocarbonylmethyl]piperazine.

(c) Repeating the procedure of Subpart (a) of this Example in a similar manner and substituting a stoichiometrically equivalent amount of alkyl anhydride for acetic anhydride and 1-[2-(optionally substituted-1,4-benzodioxan-2-yl)-2-hydroxyethyl]-4-[(optionally substituted phenyl)aminocarbonylmethyl]piperazine for 1-[2-(1,4-benzodioxan-2-yl)-2-hydroxyethyl]-4-[(2,6-dimethylphenyl)aminocarbonylmethyl]piperazine, there is obtained the corresponding 1-[2-(optionally substituted-1,4-benzodioxan-2-yl-2-alkanoyloxyethyl]-4-[(optionally substituted phenyl)aminocarbonylmethyl]piperazine.

(d) The compounds described in Subparts (a), (b), or (c) of this Example when treated with excess hydrochloric acid as described in Example 8 produce the corresponding 1-[2-(optionally substituted 1,4-benzodioxan-2-yl)-2-alkanoyloxyethyl]-4-[(optionally substituted phenyl)aminocarbonylmethyl]piperazine dihydrochloride.

In all preparations decsribed by Subparts (a), (b), (c) and (d) of this Example, the stereochemistry of the compound of formula I is not changed.

EXAMPLE 13

The following example illustrates the preparation of representative pharmaceutical formulations containing an active compound of formula I, e.g., 1-[2-(1,4-benzodioxan-2-yl)-2-hydroxyethyl]-4-[(2,6-dimethylphenyl)aminocarbonylmethyl]piperazine.

| I.V. Formulation | |
|---|---|
| Active compound | 0.14 g |
| Propylene glycol | 20.0 g |
| POLYETHYLENE GLYCOL 400 | 20.0 g |
| TWEEN 80 | 1.0 g |
| 0.9% Saline solution | 100.0 ml |

In Examples 14 through 20, the active ingredient is 1-[2-(1,4-benzodioxan-2-yl)-2-hydroxyethyl]-4-[(2,6-dimethylphenyl)aminocarbonylmethyl]piperazine dihydrochloride. Other compounds of formula I and the pharmaceutically acceptable salts thereof may be substituted therein.

EXAMPLE 14

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 15

| Ingredients | Quantity per capsule, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 16

| Ingredients | Quantity per tablet, mgs. |
|---|---|
| Active ingredient | 1 |
| cornstarch | 50 |
| lactose | 145 |
| magnesium stearate | 5 |

The above ingredients are mixed intimately and pressed into single scored tablets.

EXAMPLE 17

| Ingredients | Quantity per capsule, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 18

| Ingredients | Quantity per capsule, mgs. |
|---|---|
| Active ingredient | 150 |
| lactose | 92 |

The above ingredients are mixed and introduced into a hard-shell gelatin capsule.

EXAMPLE 19

An injectable preparation buffered to a pH of 7 is prepared having the following composition:

| Ingredients | |
|---|---|
| Active ingredient | 0.2 g |
| $KH_2PO_4$ buffer (0.4 M solution) | 2 ml |
| KOH (1 N) q.s. to | pH 7 |
| water (distilled, sterile) q.s. to | 20 ml |

EXAMPLE 20

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water q.s. to | 100 ml |

While the present invention has been described with reference to the specific embodiments thereof, it should be understood by those skilled in this art that various changes may be made and equivalents may be substituted without departing from the true spirit and scope of the invention. In addition, many modifications may be made to adopt a particular situation, material, or composition of matter, process, process step or steps, or the present objective to the spirit and scope of the invention. In addition, many modifications may be made to adopt a particular situation, material, or composition of matter, process, process step or steps, or the present objective to the spirit of this invention without departing from its essential teachings.

What is claimed is:

1. A compound of the formula:

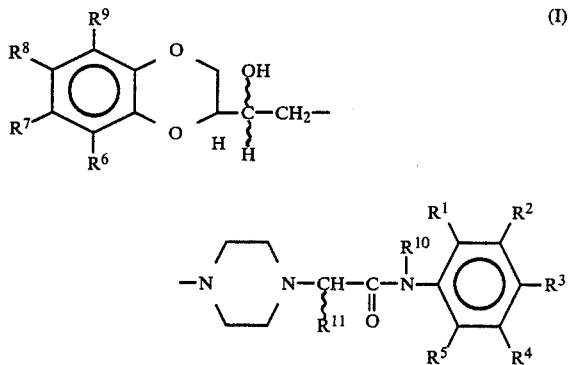

(I)

and the pharmaceutically acceptable esters and acid addition salts thereof, wherein:

$R^1$, $R^2$, $R^3$, $R^4$, $R^5$, $R^6$, $R^7$, $R^8$ and $R^9$ are each independently hydrogen, lower alkyl, lower alkoxy, trifluoromethyl, halo, lower alkylthio, lower alkyl sulfinyl or lower alkyl sulfonyl; or $R^2$ and $R^3$ together form —OCH$_2$O—; and $R^{10}$ and $R^{11}$ are each independently hydrogen or lower alkyl.

2. The compound of claim 1 wherein $R^6$, $R^7$, $R^8$ and $R^9$ are each hydrogen.

3. The compound of claim 2 wherein $R^{10}$ is hydrogen.

4. The compound of claim 3 wherein $R^{11}$ is hydrogen.

5. The compound of claim 4 wherein $R^1$ to $R^5$ are each hydrogen, i.e., 1-[2-(1,4-benzodioxan-2-yl)-2-hydroxyethyl]-4-(phenylaminocarbonylmethyl)piperazine, and the pharmaceutically acceptable esters and acid addition salts thereof.

6. The compound of claim 4 wherein $R^1$ and $R^5$ are methyl and $R^2$, $R^3$ and $R^4$ are each hydrogen, i.e., 1-[2-(1,4-benzodioxan-2-yl)-2-hydroxyethyl]-4-[(2,6-dimethylphenyl)aminocarbonylmethyl]piperazine, and the pharmaceutically acceptable esters and acid addition salts thereof.

7. The compound of claim 4 wherein $R^3$ is chloro and $R^1$, $R^2$, $R^4$ and $R^5$ are each hydrogen, i.e. 1-[2-(1,4-benzodioxan-2-yl)-2-hydroxyethyl]-4-[(4-chlorophenyl)aminocarbonylmethyl]piperazine, and the pharmaceutically acceptable esters and acid addition salts thereof.

8. The compound of claim 4 wherein $R^3$ is methyl and $R^1$, $R^2$, $R^4$ and $R^5$ are each hydrogen, i.e., 1-[(1,4-benzodioxan-2-yl)-2-hydroxyethyl]-4-[(4-methylphenyl)aminocarbonylmethyl]piperazine, and the pharmaceutically acceptable esters and acid addition salts thereof.

9. The compound of claim 4 wherein $R^3$ is methoxy and $R^1$, $R^2$, $R^4$ and $R^5$ are each hydrogen, i.e., 1-[(1,4-benzodioxan-2-yl)-2-hydroxyethyl]-4-[(4-methoxyphenyl)aminocarbonylmethyl]piperazine, and the pharmaceutically acceptable esters and acid addition salts thereof.

10. The compound of claim 4 wherein $R^1$ and $R^5$ are each chloro and $R^2$, $R^3$ and $R^4$ are each hydrogen, i.e., 1-[(1,4-benzodioxan-2-yl)-2-hydroxyethyl]-4-[(2,6-dichlorophenyl)aminocarbonylmethyl]piperazine, and the pharmaceutically acceptable esters and acid addition salts thereof.

11. The compound of claim 4 wherein $R^3$ is trifluoromethyl and $R^1$, $R^2$, $R^4$ and $R^5$ are each hydrogen, i.e. 1-[2-(1,4-benzodioxan-2-yl)-2-hydroxyethyl]-4-[(4-trifluoromethylphenyl)aminocarbonylmethyl]piperazine, and the pharmaceutically acceptable esters and acid addition salts thereof.

12. The compound of claim 4 wherein $R^1$, $R^4$ and $R^5$ to $R^9$ are hydrogen and $R^2$ and $R^3$ together form —OCH$_2$O—, i.e., 1-[2-(1,4-benzodioxan-2-yl)-2 hydroxyethyl]-4-[(3,4-methylenedioxyphenyl)aminocarboxylmethyl]piperazine, and the pharmaceutically acceptable esters and acid addition salts thereof.

13. The compound of claim 1 wherein $R^1$, $R^2$, $R^3$, $R^4$, $R^5$, $R^6$, $R^7$, $R^9$, $R^{10}$ and $R^{11}$ are hydrogen; and $R^8$ is methylsulfinyl; i.e., 1-[2-(6-methylsulfinyl-1,4-benzodioxan-2-yl)-2-hydroxyethyl]-4-[(phenyl)aminocarbonylmethyl]piperazine, and the pharmaceutically acceptable esters and acid addition salts thereof.

* * * * *